US012748020B2

(12) United States Patent
Koehl et al.

(10) Patent No.: US 12,748,020 B2
(45) Date of Patent: Sep. 29, 2026

(54) AUTONOMOUS REAL-TIME EMISSIONS MONITOR FOR MARINE EXHAUST EMISSIONS

(71) Applicant: SeaArctos Holdings LLC, New York, NY (US)

(72) Inventors: Andrew Koehl, Kowloon City (HK); Ashley Wilks, Stamford, CT (US); Robert MacBlane, Farmington, NY (US); Michael Allen, Shortsville, NY (US); Shannon Mackey, Jacksonville, NY (US); John Kulukundis, Greenwich, CT (US)

( * ) Notice: Subject to any disclaimer, the term of this patent is extended or adjusted under 35 U.S.C. 154(b) by 280 days.

(21) Appl. No.: 18/687,701

(22) PCT Filed: Aug. 31, 2022

(86) PCT No.: PCT/US2022/075750
§ 371 (c)(1),
(2) Date: Feb. 28, 2024

(87) PCT Pub. No.: WO2023/034857
PCT Pub. Date: Mar. 9, 2023

(65) Prior Publication Data

US 2024/0393214 A1 Nov. 28, 2024

Related U.S. Application Data

(60) Provisional application No. 63/238,923, filed on Aug. 31, 2021.

(51) Int. Cl.
*G01N 1/22* (2006.01)
*G01N 33/00* (2006.01)

(52) U.S. Cl.
CPC ......... *G01N 1/2247* (2013.01); *G01N 33/004* (2013.01); *G01N 33/0042* (2013.01)

(58) Field of Classification Search
CPC ...... B63B 79/10; B63B 79/30; G01M 15/102; G01M 15/108; G01M 15/106;
(Continued)

(56) References Cited

U.S. PATENT DOCUMENTS 5,060,505 A 10/1991 Tury et al.
2010/0206042 A1* 8/2010 Johns .................. G01M 15/108 73/23.31
(Continued)

FOREIGN PATENT DOCUMENTS

CN 105865853 B * 4/2020 ............. G01N 21/01
CN 213875152 U 8/2021

OTHER PUBLICATIONS

International Search Report for PCT/US2022/075750 dated Nov. 22, 2022.

*Primary Examiner* — John E Breene
*Assistant Examiner* — Truong D Phan
(74) *Attorney, Agent, or Firm* — Kilpatrick Townsend & Stockton LLP

(57) ABSTRACT

An emissions sampling apparatus for sampling from an exhaust stack of a maritime vessel to aid in regulator and efficiency monitoring of the maritime vessel. The emissions sampling apparatus including an exhaust sample intake apparatus mounted within the exhaust stack and connected to an emissions sensor apparatus mounted to the outer circumference of the exhaust stack.

14 Claims, 27 Drawing Sheets

(58) Field of Classification Search

CPC .. G01N 1/2205; G01N 1/2214; G01N 1/2247; G01N 1/2252; G01N 1/2258; G01N 1/24; G01N 1/44; G01N 2001/021; G01N 33/0037; G01N 33/004; G01N 33/0042; G01N 33/0004; G01N 33/0011; G01N 2001/2261; G01N 1/2202; G01N 2001/2255; G01N 1/22; B63H 21/32; F01N 13/008; F01N 11/00; F01N 2240/22; F01N 2250/14; F01N 2560/027; F01N 2570/04; F01N 2590/02; F01N 2590/00

USPC .............. 73/863.23, 863.81, 863.92, 864.21, 73/864.31, 114.71

See application file for complete search history.

(56) References Cited

U.S. PATENT DOCUMENTS

| | | | | |
|---|---|---|---|---|
| 2016/0348561 | A1* | 12/2016 | Higashi | F01N 11/007 |
| 2019/0339172 | A1* | 11/2019 | Sunada | B01D 53/266 |
| 2020/0264149 | A1 | 8/2020 | Kester et al. | |
| 2020/0309754 | A1 | 10/2020 | Mackey | |

* cited by examiner

AUTONOMOUS REAL-TIME EMISSIONS MONITOR FOR MARINE EXHAUST EMISSIONS

CROSS-REFERENCE TO RELATED APPLICATIONS

This application claims one or more inventions which were disclosed in Provisional Application No. 63/238,923, filed Aug. 31, 2021, entitled "AUTONOMOUS REAL-TIME EMISSIONS MONITOR FOR MARINE EXHAUST EMISSIONS". The benefit under 35 USC § 119 (e) of the United States provisional application is hereby claimed, and the aforementioned application is hereby incorporated herein by reference.

BACKGROUND

The present invention relates to environmental sensors, and more specifically to using sensors for autonomous real-time emissions monitoring of exhaust gases associated with marine engines.

The maritime shipping industry is subject to the International Maritime Organization (IMO) regulations regarding exhaust emissions. The coast guards around the world, tasked with enforcing these regulations, have few options to detect noncompliance. Those that exist are expensive and provide only very limited coverage. The US Coast Guard (USCG) and British Marine and Coastguard Agency (MCA) Coast Guards, among others, have stated publicly that they have no effective means to monitor compliance, and desire a system to help them identify which ships need scrutiny. The regulations are scheduled to become more stringent on Jan. 1, 2020.

SOx exhaust emissions, barring any mitigation process such as exhaust gas cleaning systems, correlate directly to the sulfur content in the fuel. Effectively, the fuel sulfur concentration becomes a proxy for the exhaust sulfur concentration, and the fuel switching regulations reflect this understanding.

The regulations require ships without exhaust gas cleaning systems to switch to a compliant fuel for the zone they are in, and that a record be kept of the compliant behavior. The laws require that ships burn different concentrations of low sulfur fuel inside and outside of $SO_2$ Emissions Control Area (SECA) zones, and that a log of the fuel switch events are kept for review during inspections. Confirming that a fuel switch actually did happen when the log stated that it did is a lengthy and imprecise process, upon which fines and incarceration are weighed against.

Various attempts at "sniffing" the air over ships to detect suspect ships, whether with drones, planes, or bridge mounted sensors has proven tenuous, of limited range, and often expensive.

Permanent ship-mounted sensors are globally effective. However, laboratory grade sensing devices accurate enough to match fuel testing are exceedingly expensive to install and maintain—an untenable situation for consideration as a mandatory application.

This situation leaves the Coast Guards of the world with no effective way to know where to focus their attention.

Other environmentally important gas/vapor emissions could be considered due to the differences in combustion dynamics between liquified natural gas burning engines and conventional hydrocarbon marine fuel-oil burning engines, or other alternative fuels, namely gas/vapor emissions of carbon oxides ($CO_x$), sulfur oxides ($SO_x$), nitrogen oxides (NOx), particulates (PMs), volatile organic chemicals (VOCs), hydrocarbons. Further, these trace emissions can provide information regarding the engine condition/state with regard to optimized performance. It is noted that while an exhaust scrubber will remove a portion of sulfur dioxide ($SO_2$) on a vessel's exhaust, the scrubber does not remove all of the exhausted $SO_2$. While catalytic systems remove most of NOx, the systems do not remove all of them and the systems can become overwhelmed when burning some fuels, such as biofuels.

SUMMARY

According to one embodiment of the present invention, a marine exhaust stack emissions sensor useful for regulatory and efficiency monitoring.

According to another embodiment, an emissions sampling apparatus for sampling from an exhaust stack of a maritime vessel is disclosed. The emissions sampling apparatus comprise an exhaust sample intake apparatus and an emissions sensor apparatus. The exhaust sample intake apparatus is mounted within the exhaust stack and comprises: an exhaust inlet for receiving exhaust gas from within the exhaust stack; an exhaust sample particulate filter within the exhaust inlet for removing particulates from the exhaust gas; a gas sample channel connected to an exhaust sample particulate filter outlet; and a gas sample tube with a first end connected to the gas sample channel and a second end.

The emissions sensor apparatus is mounted to an outer circumference of the exhaust stack of the maritime vessel and comprises: a condenser, a gas drying tube, at least one gas absorption cell, a pump, a processor, and a thermoelectric generator assembly.

The condenser is connected to the second end of the gas sample tube to separate and discharge condensate from the exhaust gas, with the condenser comprising: a condenser chamber having a gas input, a gas output and a condensation output; a condenser block surrounding the condenser chamber to cool exhaust gas in the condenser chamber; an exhaust gas export valve connected to the gas output of the condenser chamber; and a condensation discharge port valve connected to the condensation output to remove condensate from the exhaust gas.

The gas drying tube is connected to the gas output of the condenser chamber. The gas drying tube comprising: a first hollow tube having a first hollow tube inlet connected to the gas output of the condenser chamber and a first hollow tube outlet connected to a particulate filter; and a second hollow tube surrounding the first hollow tube, the second hollow tube having a second hollow tube inlet and a second hollow tube outlet connected to a gas exit.

The at least one gas absorption cell determines sulfur dioxide and carbon dioxide levels within the exhaust gas. The at least one gas absorption cell comprising: an inlet connected to the outlet of the particulate filter and an exhaust outlet for exhausting gas to the second hollow tube inlet of the gas drying tube, the gas absorption cell having a first end with an emitter comprising a reflector and an infrared source, a second end with at least one detector and at least two passband filters with one of the passband filters specific to carbon dioxide and another of the passband filters specific to sulfur dioxide, the first end of the gas absorption cell and the second end of the gas absorption cell being separated by a sample gas chamber extending a length between the first end of gas absorption cell and the second end of gas absorption cell.

The pump pumps the exhaust gas from the exhaust gas of the maritime vessel through the exhaust sample intake, the condenser, the first hollow tube of the gas drying tube, the particulate filter, the gas absorption cell, the second hollow tube of the gas drying tube and out the exhaust outlet.

The exhaust gas from the exhaust outlet of the at least one gas absorption cell is pumped by the pump through the second hollow tube to the gas exit, such that a water vapor content of the exhaust gas pumped through the second hollow tube has less than a water vapor content than the exhaust gas flowing through the first hollow tube. The exhaust gas in the first hollow tube transfers water vapor through walls of the first hollow tube to the exhaust gas in the second hollow tube drying the exhaust gas. The exhaust gas from the first hollow tube outlet contains less water vapor than the exhaust gas at the first hollow tube inlet.

The thermoelectric generator assembly harvesting energy from heat off of the exhaust stack, with the thermoelectric generator assembly comprising: a thermal transfer pad having a first side adjacent the outer circumference of exhaust stack and a second side; a thermal transfer block attached to the second side of the thermal transfer pad; a heat sink comprising a plurality of fins on a dissipation side; a thermoelectric generator between the heat sink and the thermal transfer block; at least one screw securing the heat sink to the thermal transfer block; and a spring between the at least one screw and the heat sink.

DETAILED DESCRIPTION

Figure 1:
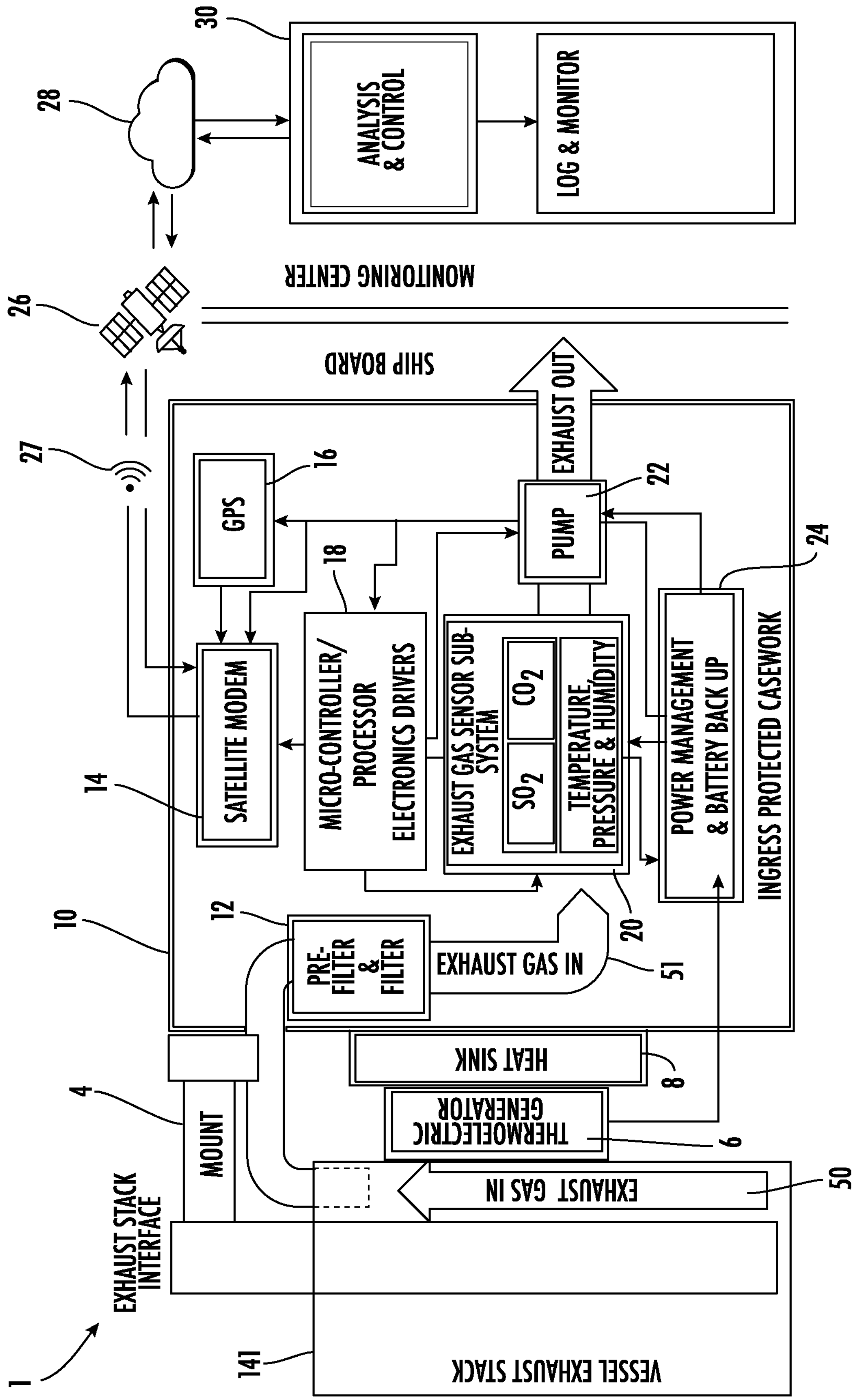
FIG. 1 shows an overview of the maritime sulfur dioxide emissions switch monitoring system.
Figure 2B:
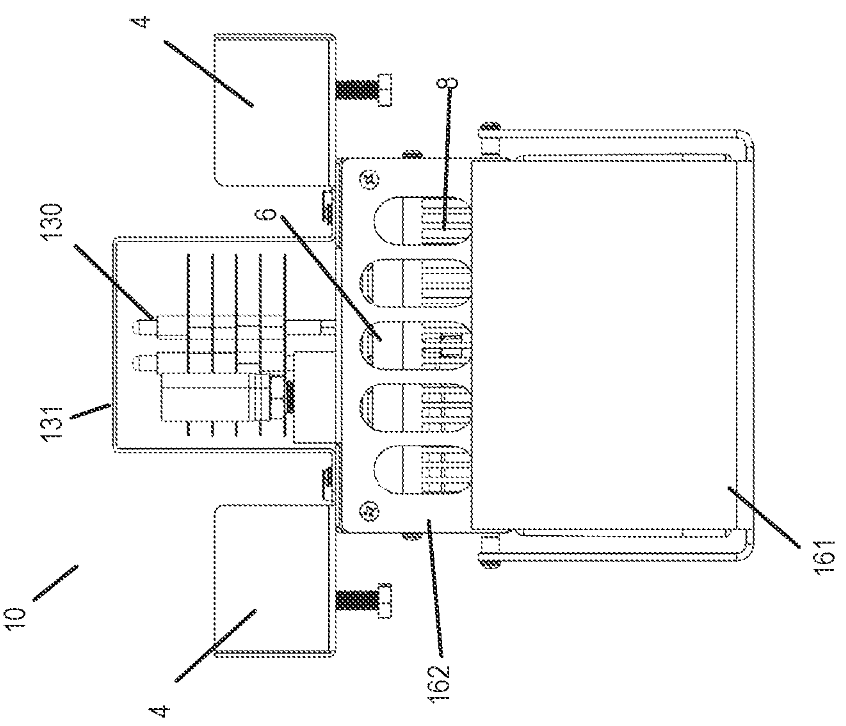
FIG. 2*b* shows a top view of the sulfur dioxide emissions apparatus.
Figure 2A:
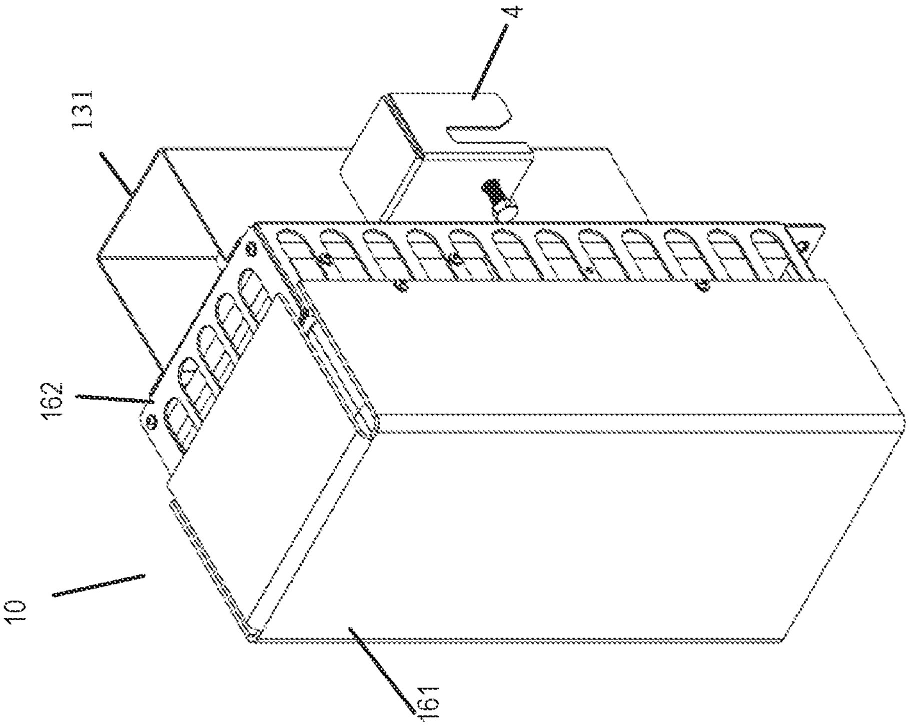
FIG. 2*a* shows an isometric view of the sulfur dioxide emissions apparatus.
Figure 2D:
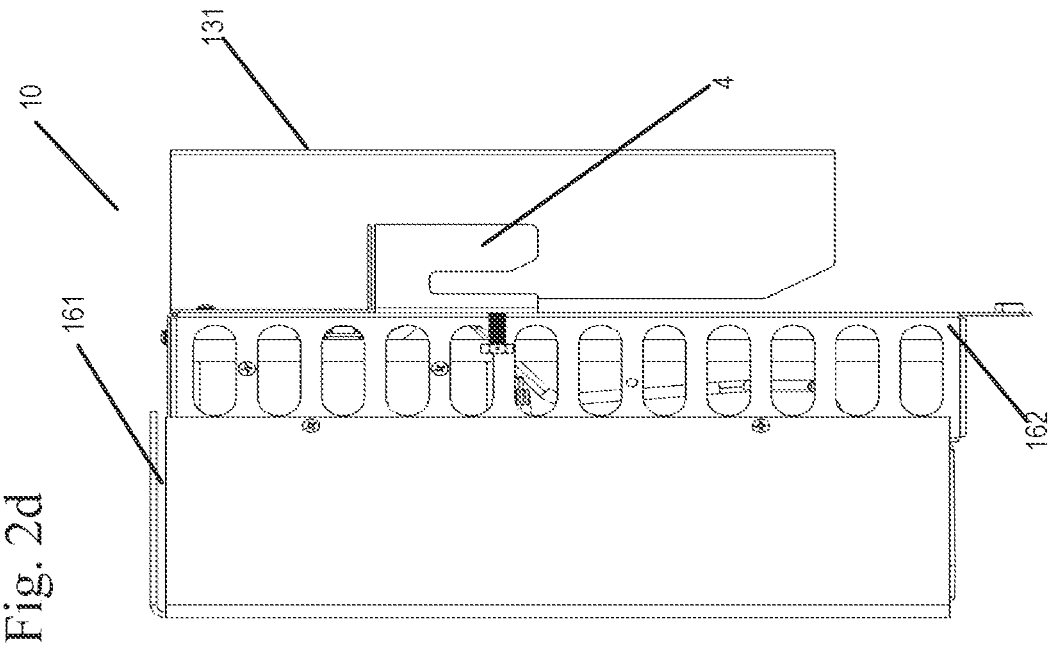
FIG. 2*d* shows a side view of the sulfur dioxide emissions apparatus.
Figure 2C:
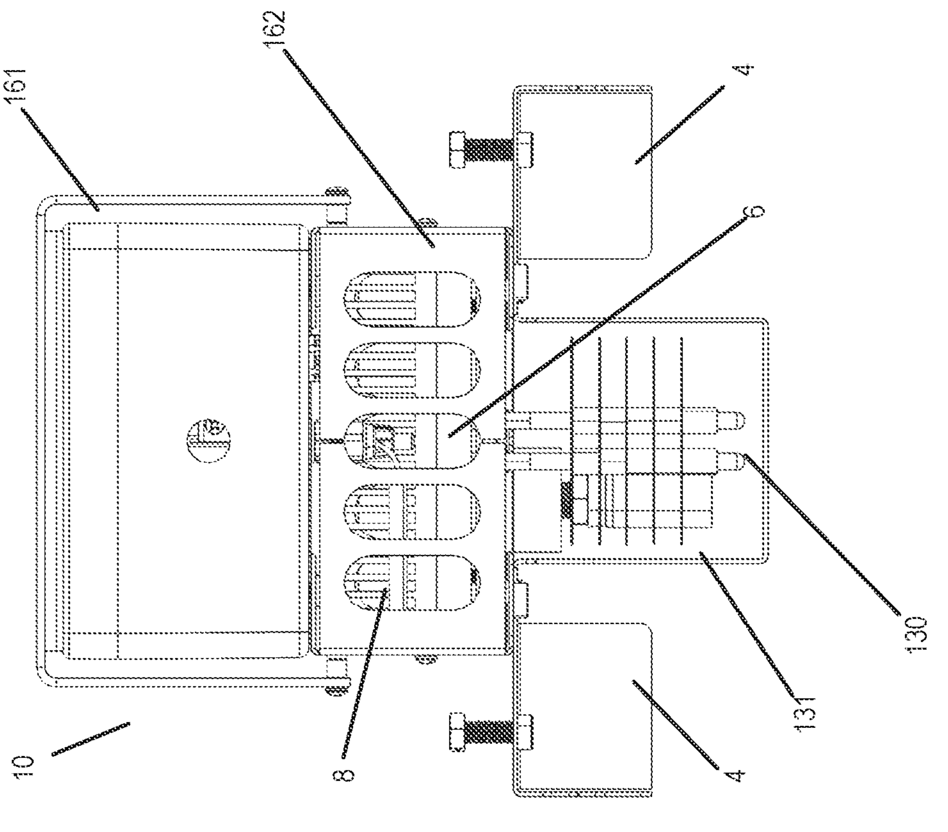
FIG. 2*c* shows a bottom view of the sulfur dioxide emissions apparatus.
Figure 2E:
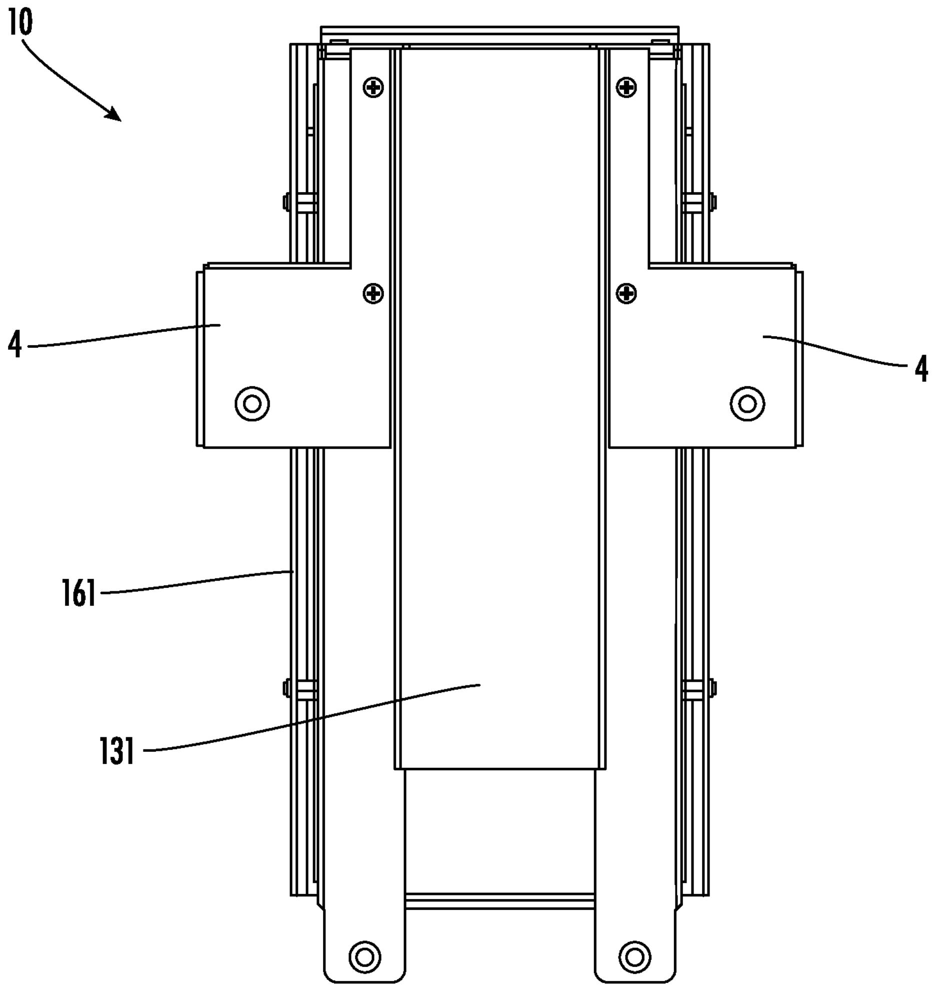
FIG. 2*e* shows a back view of the sulfur dioxide emissions apparatus.

In an embodiment of the present invention, stack exhaust gas of a maritime vessel is sampled at preprogrammed intervals and preconditioned in a prefilter to eliminate particulate matter (PM) and equilibrate Water Vapor Content (WVC) to the local ambient environment. Sampling is driven by a pump, which pulls exhaust gases through an exhaust gas sensor subsystem of an emissions sampling apparatus. The exhaust gas sensor subsystem measures combustion products. For example the combustion products can include: methane, sulfur dioxide, carbon dioxide, nitrogen dioxide, nitrogen oxide, carbon monoxide, and hydrocarbons of ethane, propane, isopropane, butane.

The combustion products can be measured by means of a Non-Dispersive InfraRed Absorption Spectrometry (NDIR-AS) tuned to respond at respective band centers of methane ($CH_4$), nitrogen dioxide ($NO_2$), nitrogen oxide (NO), carbon monoxide (CO), Hydrocarbons (HC), carbon dioxide ($CO_2$) and sulfur dioxide ($SO_2$) in the mid-IR spectral band. Non-target gas specific reference bands are used for internal reference and for WVC background correction in the $SO_2$ detection band. The emissions sampling apparatus is self-powered by a Thermo-electric Generator (TEG), which is driven by the temperature differential between the exhaust stack gas and an ingress protected exhaust gas sensor subsystem. The TEG also serves to maintain charge of a back-up battery that powers the emissions sampling apparatus when the TEG cannot deliver, for example due to low or absent engine load when the vessel is in port. The emissions sampling apparatus is further able to automatically switch to a sleep when engine is long-term idle, awaking once again when in service. The emissions sampling apparatus additionally includes a global positioning system (GPS) and can transmits combustion product measurement data and other data at pseudo-real-time intervals over a communications link.

The emissions sampling apparatus has a small footprint, is self-powered and maintenance free.

Water Vapor Content (WVC) correction can be applied, in order to enable high accuracy quantification (to the ppm by volume level). In cases where absorption band cross-over occurs, linear algebra may be applied to determine the gas/vapor specific absorption components (and therefore individual concentration levels as ppm (v)), based on the Beer-Lambert absorption cross-section principle. Other gas sensing technologies (for example electrochemical gas sensing, surface acoustic wave detection, piezoelectric) could be implemented in the exhaust gas sample flow path to further improve quantitative accuracy, if necessary. Monitoring of PM emissions could be achieved using any number of commercial-off-the-shelf PM detection technologies, placed either in parallel to, or in series with, the incoming exhaust gas sample.

The emissions sampling apparatus preferably can determine exhaust $SO_2$ content within a range of 2-500 parts per million volume (equivalent to fuel sulfur content (FSC) of <0.1%-3.5%). This range covers the use of ultra-low sulfur fuel oil (ULSFO), very-low sulfur fuel oil (VLSFO) and through heavy fuel oil (HFO) burning under all engine load conditions. The exhaust $CO_2$ content detection range is preferably between 1 to 10% by volume.

In one embodiment, the sampling takes place an intervals of approximately 60 minutes or less or at another interval when the maritime vessel is less than 20 nautical miles from a monitoring SECA boundary. Other sampling schemes may also be implemented.

Overview

FIG. 1 shows an overview of the maritime sulfur dioxide emissions switch monitoring system 1.

An emissions sampling apparatus 10 is attached to at least one exhaust stack of a funnel on a maritime vessel through a mount 4.

Referring to FIGS. 2*a*-2*e*, the emissions sampling apparatus 10 has a housing 161 which surrounds and protects subsystems of the apparatus 10 from dirt, airborne dust particles (IP66 or NEMA 4× rated). The housing 161 is connected to a heat sink housing 162 surrounding a heat sink 8 and a thermo-electric generator (TEG) 6. The TEG 6 is connected to a heat collector 130 adjacent the mount 4 for connecting and placement of the emissions sampling apparatus 10 within the exhaust stack of the maritime vessel. The heat collector 130 may be surrounded by a heat collector housing 131. When installed on an exhaust stack, the heat collector 130 is present within an exhaust gas stream from the exhaust stack. Also present within the housing 161 is a prefilter 12, a pump 22, an exhaust gas sensor subsystem 20, electronics drivers and processors 12, a satellite modem 14, a global positioning system 16, and a power management and battery back-up system 24.

Referring back to FIG. 1, exhaust gas 50 from the exhaust stack is pumped by pump 22 through an inlet of the prefilter 12 of the emissions sampling apparatus 10. The prefilter 12 also includes a condenser element discussed in further detail below. After the exhaust gas 51 has passes through the prefilter 12, the gas enters the exhaust gas sensor subsystem 20 which measures at least sulfur dioxide content, carbon dioxide content, temperature of the exhaust gas, pressure of the exhaust gas, and relative humidity. The exhaust gas 52 is then pumped and exhausted out of the emissions sampling apparatus 10 via pump 22 an exhaust outlet of a gas absorption cell of the exhaust gas sensor subsystem 20.

The emissions sampling apparatus 10 additionally has electronic drivers and processors 18 to control, process and store data from the exhaust gas sensor subsystem 20, the pump 22, and the satellite modem 14. The pump 22, the electronic drivers and processors 12, and the exhaust gas sensor subsystem 20 are additionally connected to a power management and battery back-up system 24 in communication with the TEG 6 for power supply.

Location from a global position system (GPS) 16 is also provided to the satellite modem 14 to send with other data to the monitoring center 30 over a network 28. The network 28 may comprise copper wires, optical fibers, wireless transmission, routers, firewalls, switches, gateway computers and/or edge servers.

The emissions sampling apparatus 10 on the maritime vessel is in communication via a network 28 through satellite 26 and/or wireless communication 27 with the monitoring center 30.

Thermo-Electric Generator (TEG)

Figure 9:
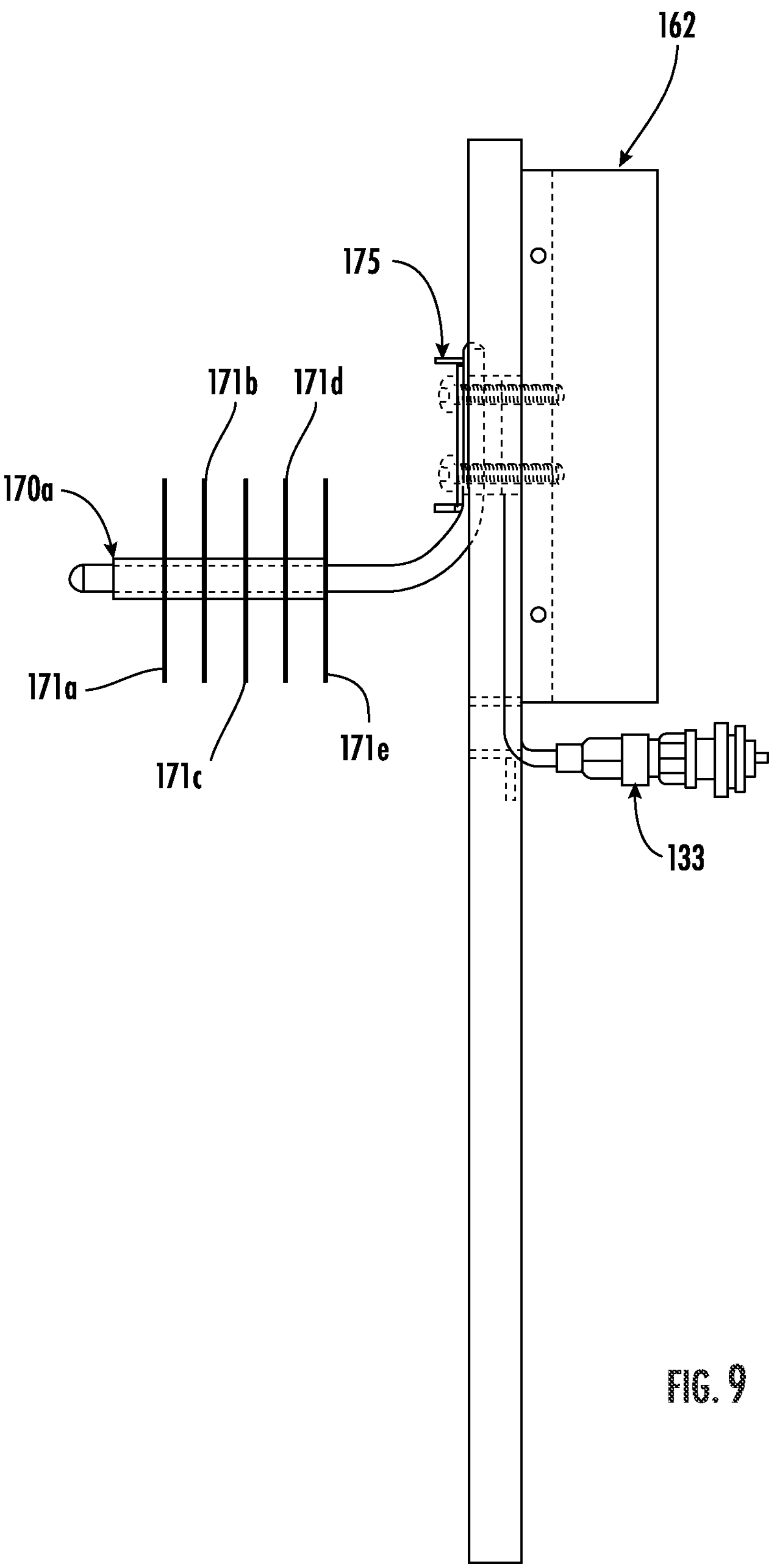
FIG. 9 shows a side view of the heat sink.
Figure 10:
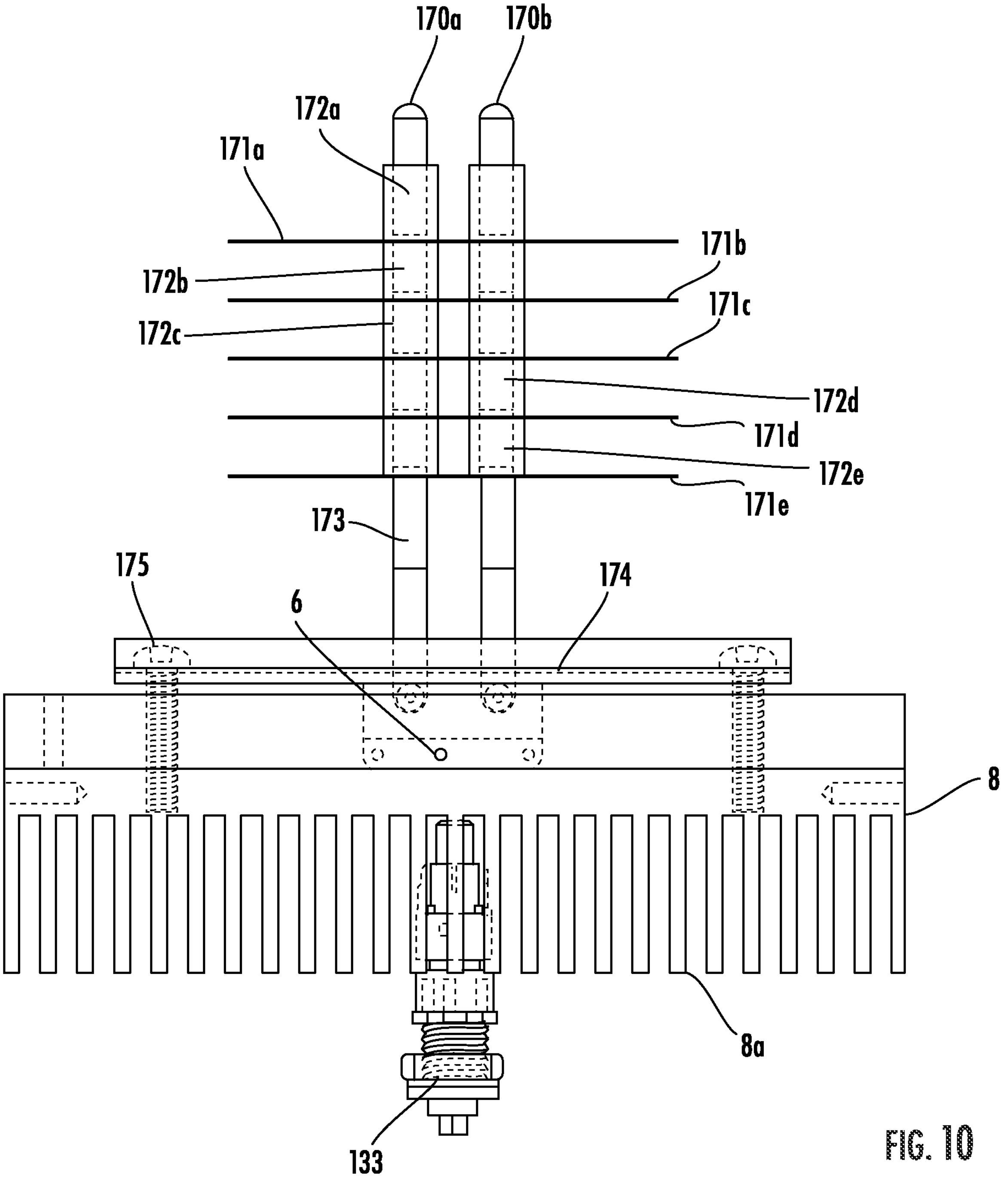
FIG. 10 shows a top view of the thermoelectric generator (TEG) and the heat sink.

Referring to FIGS. 9 and 10, within the heat sink housing 162 is a thermo-electric generator (TEG) 6, and a heat sink 8. The output of the TEG 6 and heat sink 8 is a power source connector 133 supplying power to the power management and back-up system 24 to power the emissions sampling apparatus 10.

The heat collector 130 is fixed to the heat sink housing 162 and the TEG 6, for example using clamps and screws 175 to hold the heat collector 130 and TEG 6 together with minimal separation. Insulation may be present between the heat collector 130 and the heat sink housing 162. The heat collector 130 is placed within the exhaust gas of the exhaust stack. The heat collector 130 includes at least two heat pipes 170*a*, 170*b* with a plurality of fins 171*a*, 171*b*, 171*c*, 171*d*, 171*e* spaced apart by spacers 172*a*, 172*b*, 172*c*, 172*d*, 172*e*.

The internal combustion engine of the maritime vessel emits exhaust gas through the exhaust gas stacks when operating, and the exhaust gas is generally characterized as having an elevated temperature. Fins 171*a*, 171*b*, 171*c*, 171*d*, 171*e* of the heat collector 130 collect heat directly from the exhaust gas of the exhaust gas stack and transfers heat through the heat pipes 170*a*, 170*b*. From the heat pipes 170*a*, 170*b*, heat is transferred to a heat carriers 173 which transfer the heat through the heat shield 174 to the TEG 6 and the heat sink 8. The heat shield 174 is present between the heat carriers 173 and the TEG 6. The heat shield 174 blocks heat to improve the effectiveness of the heat sink 8. Heat provided to the heat sink 8 dissipates on a heat dissipation side 8*a*. The thermal carriers 173 includes two dissimilar conductors which are bounded by the exhaust gas stack at a high temperature and the heat sink 8 at a lower temperature to create electrical potential. The TEG 6 generates power while cooling and dissipation of heat through the heat dissipation side 8*a* of the heat sink 8 to create electrical potential which can be stored and transferred to the power management and battery back-up system 24 and/or directly to power the emissions sampling apparatus 10 via the connector 133. The heat sink 8 draws heat from the TEG 6.

In other embodiments, the TEG 6 can be replaced with other self-powering options, which can include and is not limited to solar power or wind power.

The power management and battery backup system 24 controls the battery charging from the TEG 8 according to the voltage and environmental specifications of the battery of the emissions sampling apparatus 10. A state of charge calculation based on voltage and current flow monitoring over time and temperature is conducted by the power management and battery backup system 24. The state of charge value allows alerts to be triggered when the battery is in defective or low charge state.

Exhaust Gas Flow

Figure 3A:
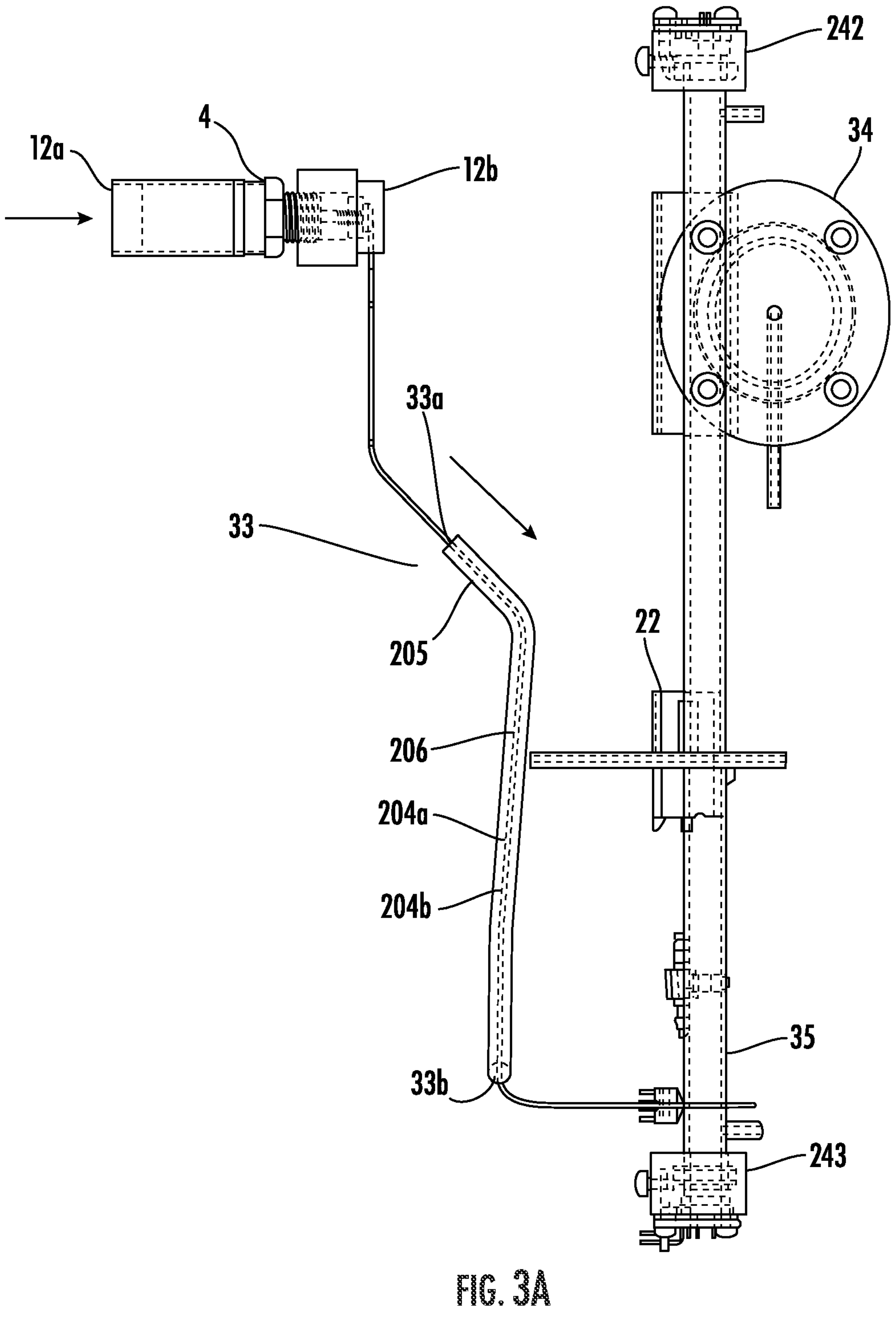
FIG. 3*a* shows a first view of the prefilter, exhaust gas filter sensor subsystem and pump of the sulfur dioxide emissions apparatus.
Figure 3B:
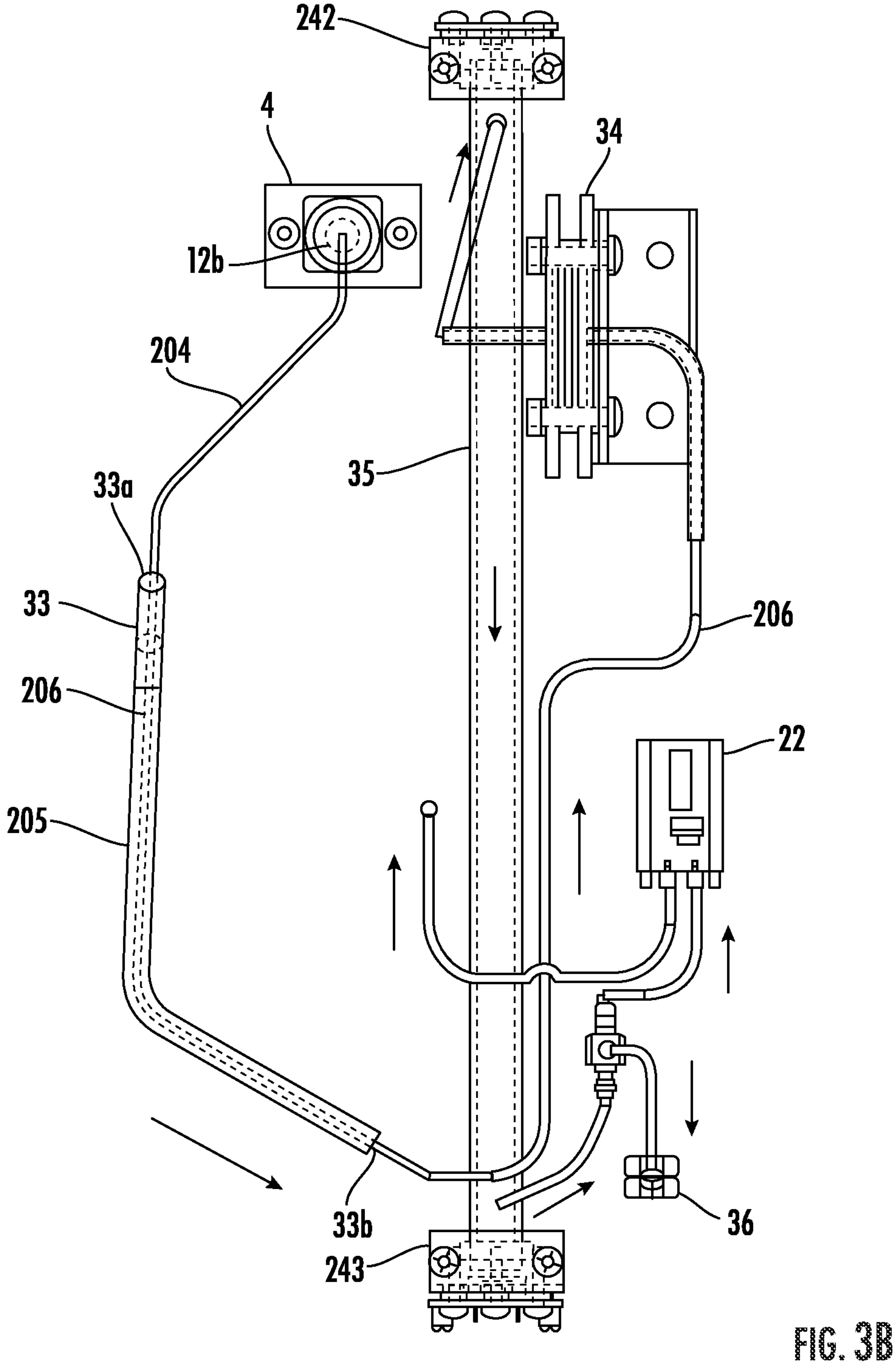
FIG. 3*b* shows an alternate view of the prefilter, exhaust gas filter sensor subsystem and pump of the sulfur dioxide emissions apparatus.

FIGS. 3*a*-3*b* show the prefilter, exhaust gas filter sensor subsystem and pump of the sulfur dioxide emissions apparatus. Exhaust gas flow is indicated by the arrows.

Generally, exhaust gas is pumped by pump 22 through the prefilter 12. From the prefilter 12, the exhaust gas travels through a condenser element 33, into layered filter 34. From layered filter 34, exhaust gas travels through a gas absorption cell 35 and exhausts out of the emissions sampling apparatus 10. A pressure/temperature sensor 36 is present between the gas absorption cell 35 and the pump 22.

Prefilter

Figure 4:
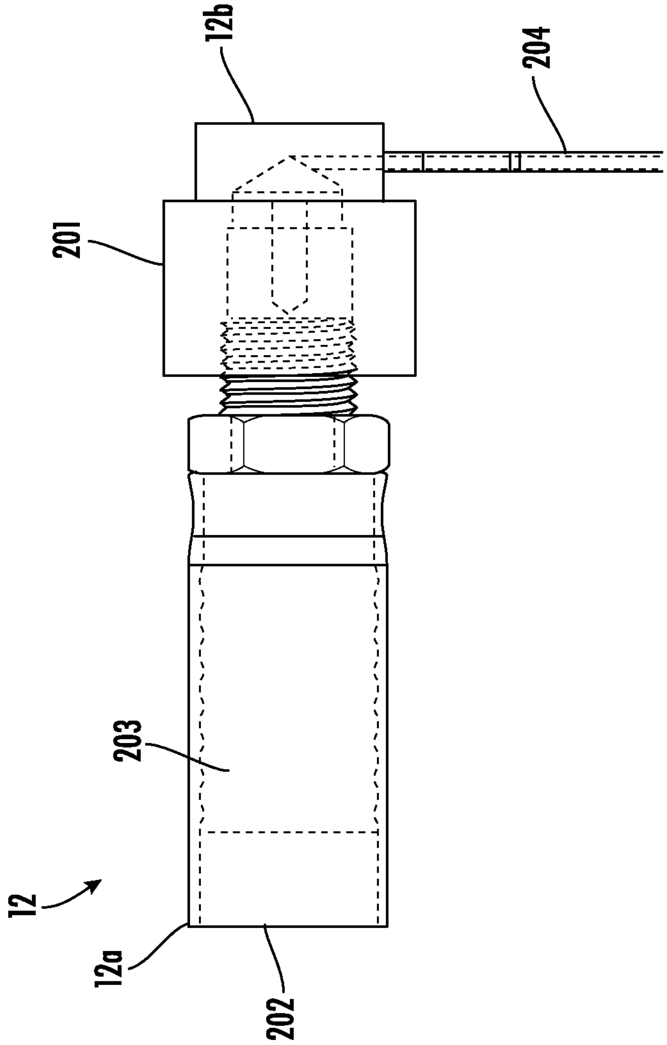
FIG. 4 shows a closeup of the prefilter of FIGS. 3*a*-3*b*.

FIG. 4 shows the prefilter 12. A first end 12*a* of the prefilter 12 has an exhaust gas intake 200 and is present within the exhaust gas stack. The second end 12*b* of the prefilter 12 is in communication with a condenser element 33 via a manifold 201, preferably made of stainless steel. The first end 12*a* has an opening 202 with a porous stainless steel filter 203 for receiving the exhaust gas intake. Exhaust gas passes through the filter 203, through the manifold 201 and into the tubing 204 connected to a first end 33*a* of a condenser element 33. The stainless steel filter 203 preferably removes particulates which are greater than 0.05 microns.

Condenser

Referring to FIGS. 3*a*-3*b*, the condenser 33 is formed of a sleeve 205 surrounding tubing 204. The tubing 204 is preferably porous allowing moisture to be transferred from the inside 204*a* of the tubing 204 to the outside 204*b* of the tubing 204. In on embodiment, the tubing 204 is made of a polymer and the sleeve 205 may be made of gore-tex or other breathable material. Ambient air through the sleeve 205 can be used to cool the exhaust gas vapor as the vapor travels through the tube 204. While not shown, water or other fluid may be circulated within the sleeve 205 to aid in cooling the exhaust gas vapor as the vapor travels through the tube 204. The exhaust gas vapor is preferably cooled below the dew point temperature of the ambient atmospheric conditions. The second end 33*b* of a condenser 33 is in communication with a layered filter 34.

Layered Filter

Figure 5A:
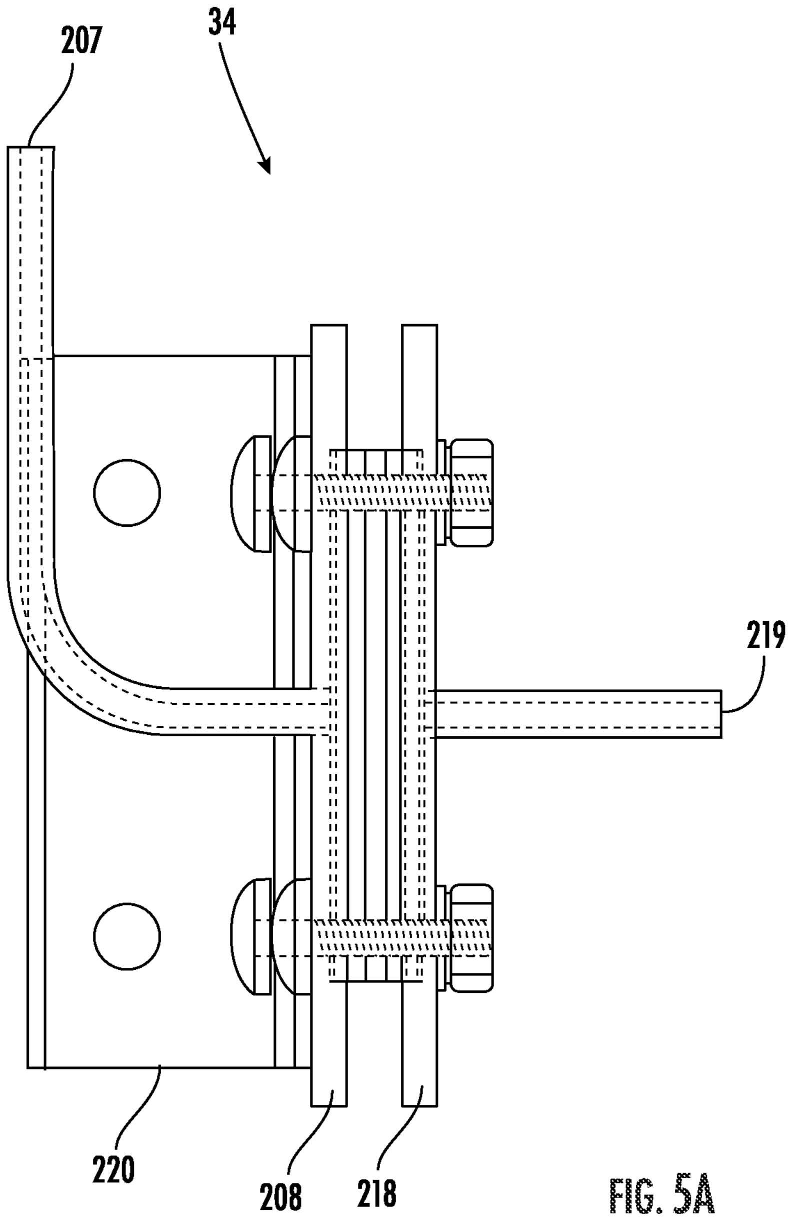
FIG. 5*a* shows a side view of the layered filter of FIGS. 3*a*-3*b*.
Figure 5B:
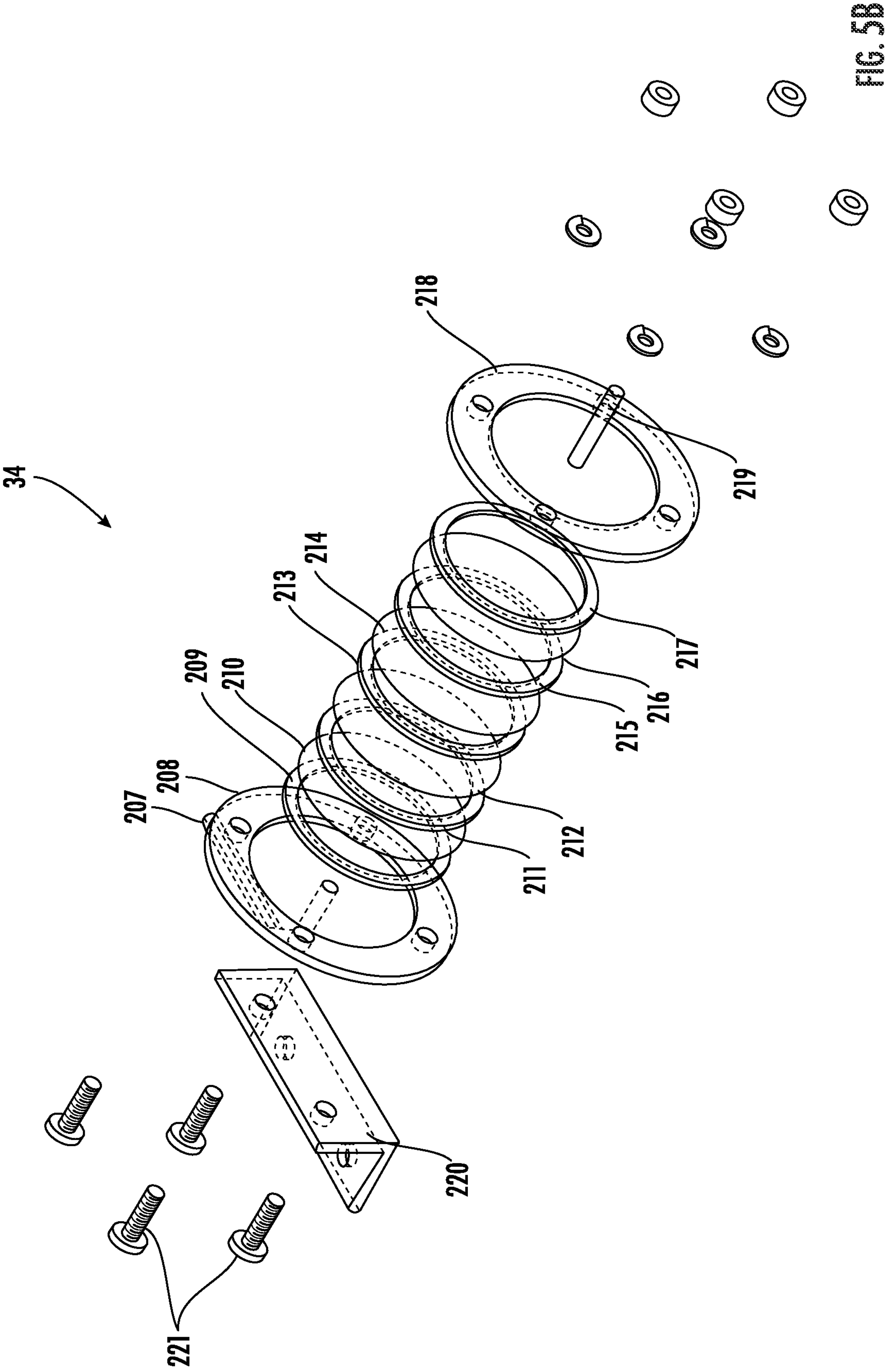
FIG. 5*b* shows an exploded isometric view of the layered filter of FIGS. 3*a*-3*b*.
Figure 5C:
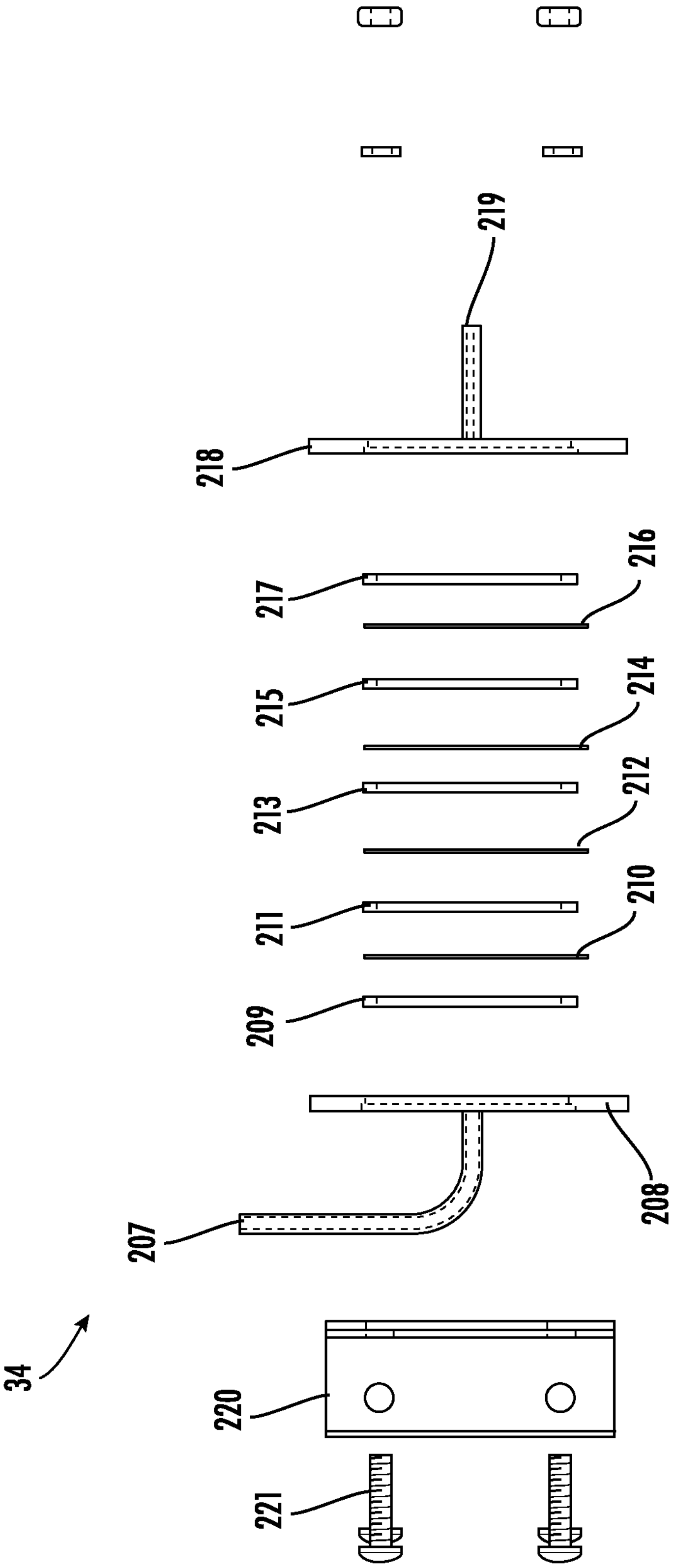
FIG. 5*c* shows an exploded side view of the layered filter of FIGS. 3*a*-3*b*.

The layered filter 34 receives the cooled air via a tube 206 through an intake 207 coupled to an intake flange 208 shown in FIGS. 5*a*-5*c*. From the intake flange 207, exhaust gas vapor passes through a first gasket 209, a first filter 210, a second gasket 211, a second filter 212, a third gasket 213, a third filter 214, a fourth gasket 215, a fourth filter 216 and a fifth gasket 217 to the exhaust through the exhaust 219 of the exhaust flange 218. The multiple gaskets 209, 211, 213, 215, 217 and filters 210, 212, 214, 216 are held in place between the exhaust flange 218 and the intake flange 208 via a plate 220 and bolts 221. The plate 220 additionally supports the pipe connection to pipe 206.

The first filter 210, second filter 212, third filter 214 and fourth filter 216 are all preferably different particle sizes. For example, the first filter 210 is a 10 μm filter, the second filter 212 is a 1.0 μm filter, the third filter 214 is a 0.45 μm filter and the fourth filter 216 is a wire mesh. The filter sizes can be any size that adequately eliminates the entry of particles that are greater than 2 μm to prevent infrared (IR) dispersion and eliminate as many particulates which are less than 2 μm to ensure that the gas absorption cell 240 discussed below does not suffer from precipitation of small particles within the sample chamber.

Gas Absorption Cell

Figure 6:
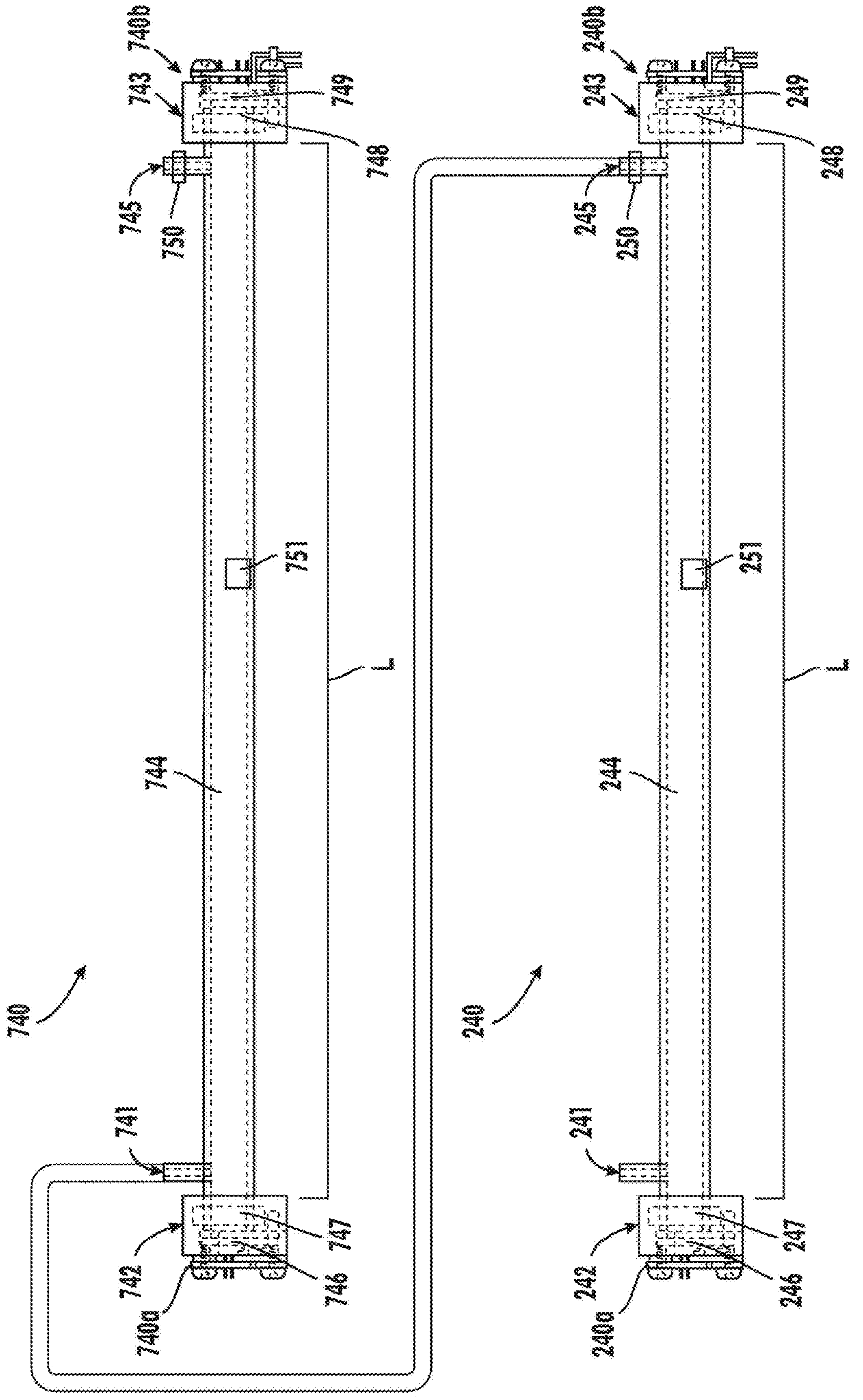
FIG. 6 shows a gas absorption cell of the exhaust gas filter sensor subsystem.

An example of the gas absorption cell 240 utilizing non-dispersive infrared absorption spectrometry (NDIR-AS) is shown in FIG. 6. From the exhaust 219 of the exhaust flange 218, exhaust gas vapor passes into the intake port 241 of the gas absorption cell 240.

The gas absorption cell 240 has a first end 240*a* with an emitter 242 and a second end 240*b* with a detector 243, and a length L between the emitter 242 and the detector 243 forming a sample chamber 244. The intake port 241 and the exhaust port 245 are between the emitter 242 and the detector 243 along the length L of the sample chamber 244 of the gas absorption cell 240. In one embodiment the sample chamber 244 has a length of at least 28.5 cm.

The emitter 240 at the first end 240*a* has a reflector 247 and an infrared source 246. The detector 243 at the second end 240*b* includes one or more passband filters 248 and an infrared detector 249. The infrared light from the infrared source 246 is directed through the sample chamber 244 towards the detector 243. Sensors 251 may be present within the sample chamber 244 for gas pressure and gas temperature. The location of the sensors 251 in FIG. 6 is for illustration purposes only and can be anywhere within the sample chamber 244. The gas in the sample chamber 244 causes absorption of specific wavelengths and the attenuation of these wavelengths is measured by the detector 243 to determine the gas concentration. One or more passband or optical filters 248 are located in front of the detector 243 to eliminate all infrared light except the wavelength that the selected gas molecules can absorb. The detector 243 measures the amount of infrared (IR) light that was not absorbed by the filters 248. After passing through the sample gas chamber 240, the exhaust gas vapor exits the gas absorption cell through the exhaust port 245.

In an embodiment of the present invention, the passband or optical filters 248 are specific to sulfur dioxide.

In another embodiment of the present invention, the passband or optical filters 248 are specific to carbon dioxide, sulfur dioxide and water.

In yet another embodiment, the passband or optical filters 248 include four filters corresponding to a carbon dioxide filter, a carbon dioxide reference filter, a sulfur dioxide filter and a sulfur dioxide reference filter.

In another embodiment a relative humidity sensor 250 is present at the exhaust port 245 to measure the water vapor content of the exhaust gas.

In an alternate embodiment, the gas absorption cell 240 has a single IR light source 246 and the detector 243 includes two detectors corresponding to two different pass-band filters 248 for different gases in front of the two detectors, for example carbon dioxide and sulfur dioxide. Infrared light that is absorbed by a target gas (e.g. sulfur dioxide or carbon dioxide) passes through the active filter with a particular bandwidth for the detection of the target gas. Infrared light that does not interact with the target gas passes through the reference filter. The difference between transmitted light intensities in these two bandwidths is converted into gas concentration. A dual wavelength sensor ensures stable measurements for a long period of operation as the aging effects of the light source or the gas cell are automatically compensated by output signals at the reference wavelength.

The filter 248 for carbon dioxide is preferably 4.45 μm with a reference of 4.65 μm. The filter 248 for sulfur dioxide is preferably 7.3 μm, with a reference of 7.85 μm. The detection of water vapor content to use a background correction is 7.85 μm with a reference of 4.65 μm.

In another embodiment, more than one filter for carbon dioxide can be present and more than one filter for sulfur dioxide can be present.

In one embodiment, the filter 248 for carbon dioxide is between 1.9-2.1 μm. In another embodiment, the filter 248 for carbon dioxide is between 2.6-2.9 μm. In yet another embodiment, the filter 248 is between 4.1-4.5 μm.

In one embodiment, the filter 248 for sulfur dioxide is between 7.1-7.6 μm.

In one embodiment, other filters can be present with various bands which are non-overlapping with carbon dioxide and sulfur dioxide or other exhaust gases, for example between 1.3-1.5 μm, 1.75-2.0 μm, 2.5-3.0 μm, and 5.0-8.0 μm.

In one embodiment, reference bands can also be present as a filter 248 which +/−0.2 μm or less than the filter. For example, a reference filter can 3.09 μm, 3.72 μm, 3.95 μm, and/or 7.85 μm.

In yet another embodiment, the single IR light source 246 comprises multiple sources with the filters 248 being adjacent the emitter and the IR light source 246.

The gas concentration is sent by the one or more detectors to the processors of the electronic drivers and processors 18. Exhaust gas 52 is then pumped out the exhaust outlet of the emissions sampling apparatus 10.

As shown in FIG. 6, multiple gas absorption cells can be present and set up serially to determine the gas concentration of different gases, such as methane, nitrogen dioxide, carbon monoxide, and hydrocarbons, including at least ethane, propane, isopropane, and butane. FIG. 6 shows an embodiment of a second gas absorption cell 740 serially connected to the gas absorption cell 240. The second gas absorption cell 740 can have similar components to the gas absorption cell 240 (7xx-series numbers refer to similar 2xx-series components described above for the gas absorption cell 240). For example, the second gas absorption cell 740 has an intake inlet 741 connected to the exhaust outlet 245 of the gas absorption cell 240, the second gas absorption cell having a first end 740*a* with an emitter 742 comprising a reflector 747 and an infrared source 746, a second end with at least one detector 743 and at least one passband filter 748 specific to any of the gases above, the first end of the second gas absorption cell 740*a* and the second end of the second gas absorption cell 740*b* being separated by a sample gas chamber 744 extending a length between the first end of the second gas absorption cell 740*a* and the second end of second gas absorption cell 740*b*. The filter for methane has a filter band center of 7.65 μm. The filter for nitrogen dioxide has a filter band center of 5.52 μm. The filter for nitrogen oxide has a filter band center of 6.21 μm. The filter for carbon monoxide has a filter band center of 4.61 μm. The filter for the hydrocarbons has filter band center of 3.40 μm.

Alternatively, the gas absorption cell can contain more than two filter and their associated reference filters.

Electronics Drivers/Processors

The processors 18 receive data associated with the exhaust gas in the stack from the gas absorption cell 240 and various sensors and sends the data associated with the gas and other data to the monitoring center 30 with the satellite modem 14. The data is preferably sent in a byte array to reduce the amount of data being sent. It is noted that the data from the emissions sampling apparatus 10 is sent to the monitoring system 30 in a regular periodic fashion whether or not it is able to communicate or spare the energy to run the communication channel, for example via the satellite modem 14.

If the satellite 26 is not available or the emissions sampling apparatus 10 does not have enough available energy to send the data, time stamped exhaust sample data is collected and stored in memory, such as one or more computer-readable RAMs 822 and one or more computer-readable ROMs 824 or one or more computer-readable tangible storage devices 830 to be uploaded at another time. The data can additionally be manually extracted from the emissions sampling apparatus 10 if necessary.

It should also be noted that the power management system 24 of the emissions sampling apparatus 10 prioritizes data collection. The power management system 24 reduces energy expenditure by stopping data transmission during low battery state.

Figure 11:
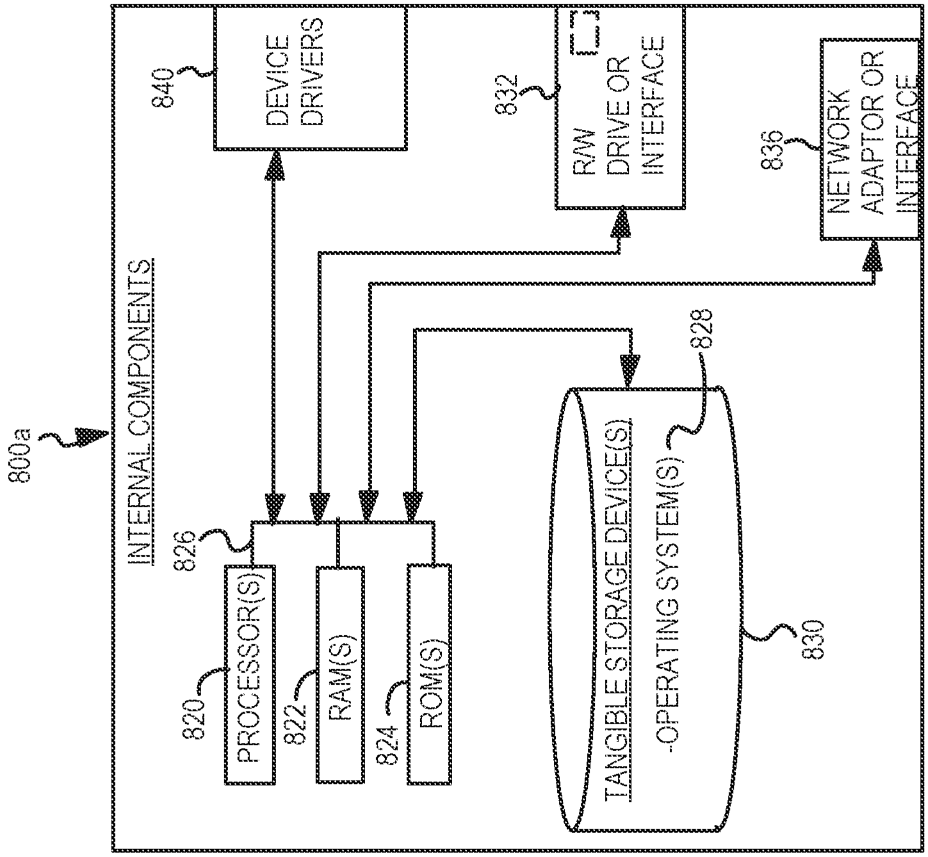
FIG. 11 illustrates internal components of the shipboard sulfur dioxide emissions apparatus and a computer associated with the monitoring center in which illustrative embodiments may be implemented.

An example of internal components associated with the electronic drivers and processors 18 are shown in FIG. 11. The electronic drivers and processors 18 can include one or more processors 820, one or more computer-readable RAMs 822 and one or more computer-readable ROMs 824 on one or more buses 826, and one or more operating systems 828 and one or more computer-readable tangible storage devices 830 as shown in FIG. 11. The one or more operating systems 828 are stored on one or more of the computer-readable tangible storage devices 830 for execution by one or more of the processors 820 via one or more of the RAMs 822 (which typically include cache memory). In the embodiment illustrated in FIG. 11, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

The internal components 800*a* also includes a R/W drive or interface 832 to read from and write to one or more portable computer-readable tangible storage devices present as part of the monitoring system 30.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language, and procedural programming languages, or similar programming languages. In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Sampling Data Collection

In an embodiment, data is collected from the exhaust gas at least every 60 minutes. The rate of collection can increase when the maritime vessel is less than 20 nautical miles from a monitoring SECA boundary.

Figure 13:
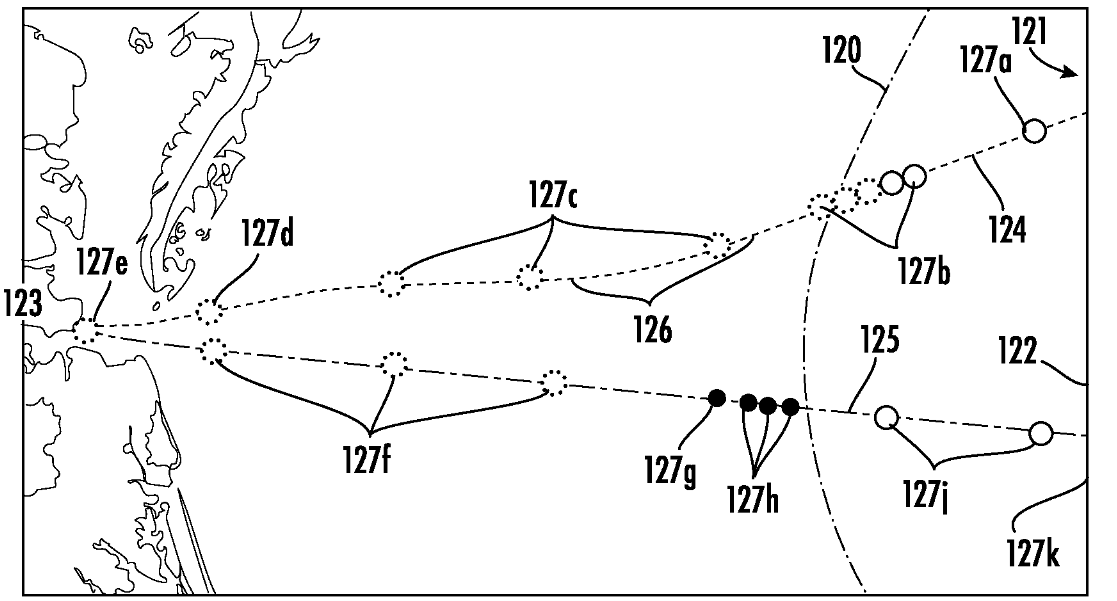
FIG. 13 shows a sketch of a sample strategy as a ship crosses a SECA boundary.

FIG. 13 shows a sketch of a sample strategy as a ship crosses a SECA boundary (dash-dot line 120) from out at sea 121 to port 123 and back to sea 122. The inbound path of the ship is represented by dashed line 124, and the outbound path of the ship is represented by short-long dash line 125. Each arrow 126 on each of the paths 124 and 125 represents approximately an hour's sailing.

The circles 127*a*-127*j* along the paths 124 and 125 represent the point at which the system takes action, which will be explained in detail in the following description. The black-filled circles 127*g*-127*h* represent readings which are out of range or "bad" (i.e. noncompliant), while the open (white-filled) circles 127*a*-127*f* and 127*j* indicate readings which are within range (i.e. compliant). Circles with dotted lines show low-emissions readings, circles with solid lines show high-emissions readings.

The exemplary strategy proceeds as follows, with the numbers referring to points on FIG. 11:

127*a*—At this point, the ship is outside the SECA boundary 120 on the inbound path 124, so high sulfur fuel is permitted. The readings from the emissions sampling apparatus 10 would be high, but still compliant, since at this point the more restricted range of the SECA does not yet apply. The system takes readings on a selected schedule, for example every hour as shown on FIG. 11. More frequent or less frequent schedules could also be chosen as appropriate. When a reading is taken, the data from the reading—for example, time, location, compliance status, and perhaps raw sensor data numbers—are stored in a repository on the ship for later transmission to the monitoring center 30 on shore.

127*b*—The ship is approaching the SECA boundary 120. The system starts taking more frequent readings, perhaps every ten minutes or more frequently, so as to capture the data showing a switch from high sulfur fuel to low sulfur fuel.

127*c*—The ship switched to low sulfur fuel as required, and the system confirms this with readings which show emissions to be compliant.

127*d*—At this point the ship is within range of the shore-based mobile telephone network. The system connects to the network and transmits a status report to the server at least indicating that the onboard system is operating OK and the ship is compliant. If desired, a full upload of data from the onboard repository could be transmitted to the central server at this time.

127*e*—The ship is in port 123. The system continues to monitor emissions to make sure it remains compliant. If it did not do so in step 127*d*, the data in the repository can be uploaded to the monitoring center 30 at this time while the ship is in port.

127*f*—The ship has left port by outbound path 125. The readings show that the emissions remain compliant with the inside-SECA standards.

127*g*—The system has detected a sample with a "bad" or out-of-range reading. It is possible that the ship has changed over to high sulfur fuel too soon, outside the SECA boundary 120, or this might be a spurious reading caused by a bad sample or transient condition.

127*h*—The system takes more frequent readings for a period, in order to confirm that the sample actually shows an uncompliant status, and is not based on spurious readings. The readings continue to be out of range, so the system logs this as a noncompliant situation.

127*j*—Since the ship is outside the SECA boundary 120, the system would be applying the higher range. The readings taken by the system are once again "good", indicating the ship is compliant with the standards applicable to this area.

127*k*—When the ship reaches its next port (off the map), all of the historical data accumulated since the last upload is transmitted from the onboard repository to the central server.

Alerts can be sent to a user on the ship with the emissions sampling apparatus 10 or an enforcement or government agency regarding compliance or noncompliance.

Mounting Options

Figure 8A:
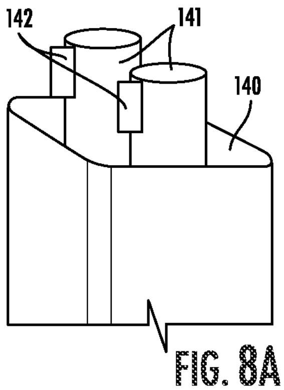
FIG. 8*a* shows a front mounting installation option on a pair of stacks of a single funnel.
Figure 8B:
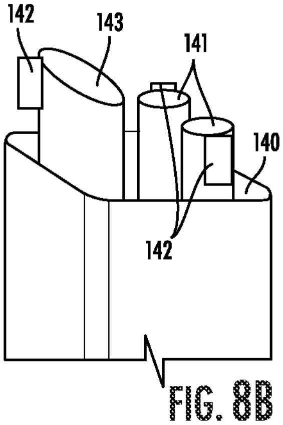
FIG. 8*b* shows outboard side installation on multiple stacks of a single funnel.
Figure 8C:
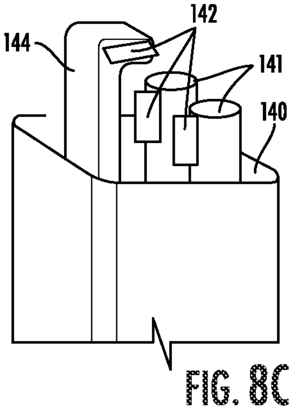
FIG. 8*c* shows mounting options on a curved exhaust stack.
Figure 8D:
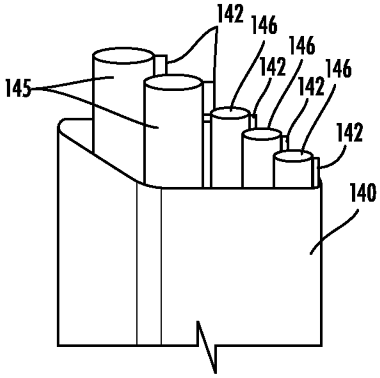
FIG. 8*d* shows a back mounting option on a plurality of stacks of a single funnel.
Figure 8E:
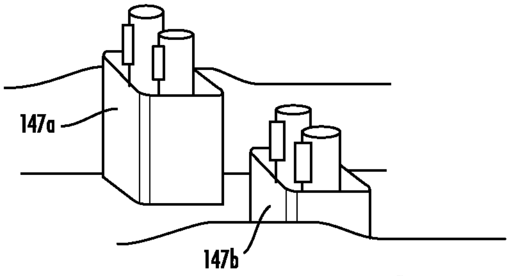
FIG. 8*e* shows multiple funnels in which multiple stacks have sensors units installed.

FIGS. 8*a*-8*f* show examples of installation options for the shipboard emissions sampling apparatus 10. In FIGS. 8*a*-8*d* and 8*f*, there is a single funnel 140 within which there are multiple exhaust stacks 141, 143, 144, 145, and 146. FIG. 8*e* shows multiple funnels 147*a* and 147*b* of the sort shown in FIG. 8*a*. In each figure, locations 142 for installing the emissions sampling apparatus 10 are indicated by boxes.

FIGS. 8*a* and 8*e* show a front mounting option, and FIG. 8*d* shows a back mounting option. FIG. 8*b* shows an outboard side installation.

FIG. 8*c* shows a ship which has a curved exhaust stack 144 in addition to two straight pipes 141. For curved pipes 144, a side mount 142 as shown would be preferred.

Figure 8F:
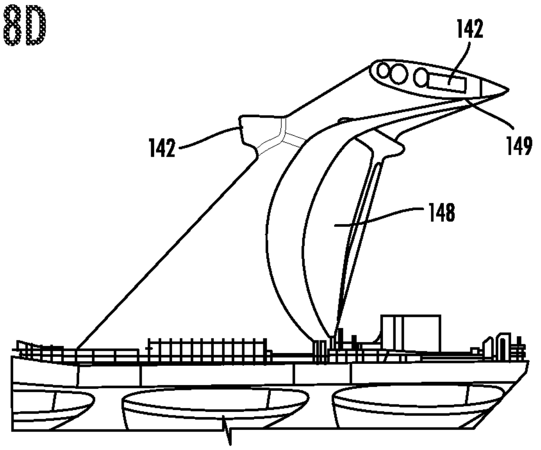
FIG. 8*f* shows a cruise ship funnel with multiple exhaust stacks and mounting of a sensor unit.

FIG. 8*f* shows a cruise ship funnel 148 of the design where multiple exhaust stacks 149 leave the funnel 148 horizontally at the ends of "wings".

Method of Autonomous Real-Time Sulfur Dioxide and Carbon Dioxide Monitoring

Figure 7:
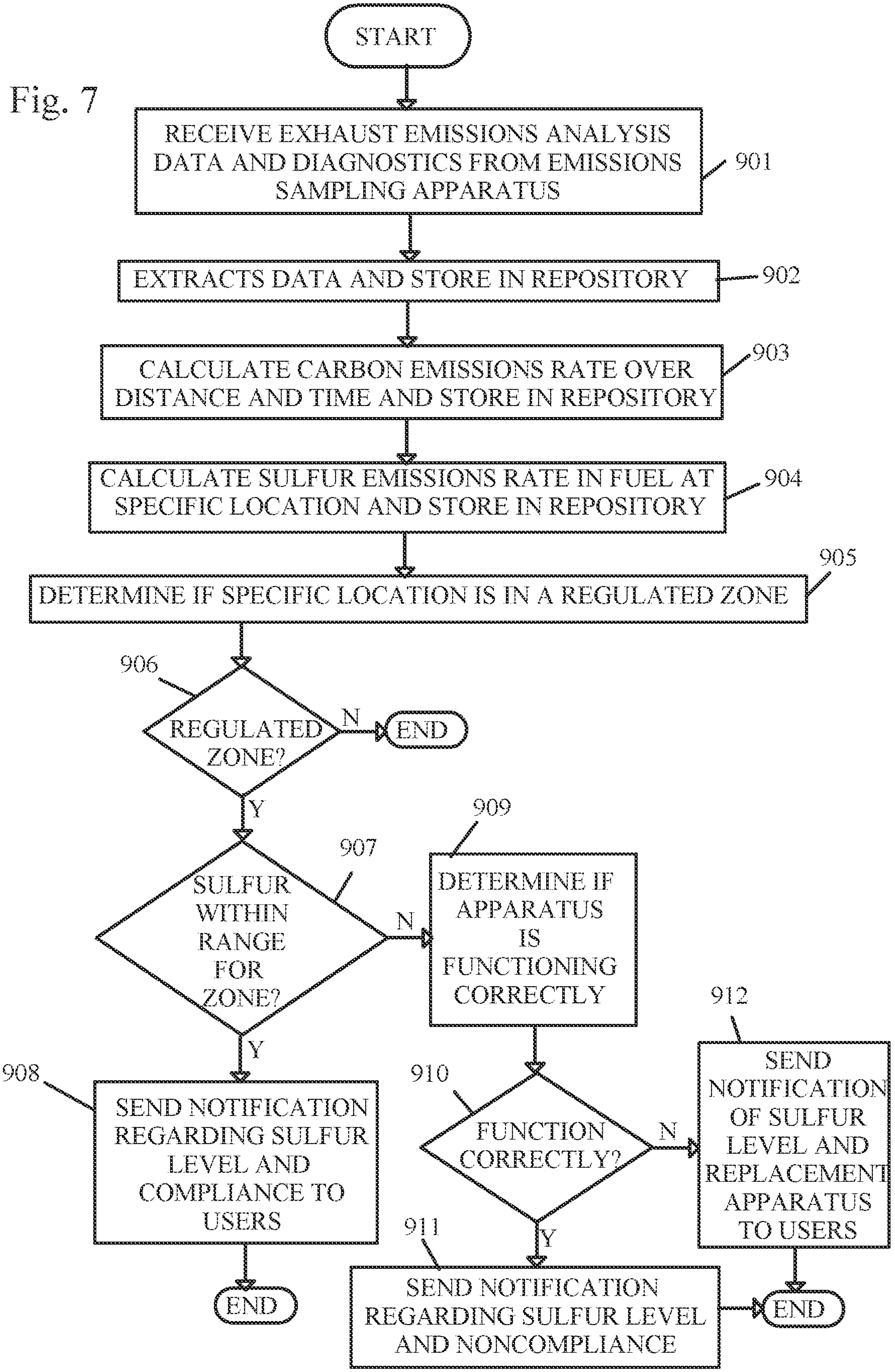
FIG. 7 shows a block diagram of a method of autonomous real-time sulfur dioxide and carbon dioxide monitoring of marine exhaust emissions.

FIG. 7 shows a method of autonomous real-time sulfur dioxide and carbon dioxide monitoring of marine exhaust emissions.

In a first step, the monitoring system of the monitoring center 30 receives exhaust emissions analysis data and diagnostics data of the maritime vessel (step 901). The data may be sent in a data array to the monitoring system.

The exhaust emissions analysis data can include: date, time, latitude and longitude, sulfur dioxide values, carbon dioxide values, gas humidity, gas pressure, altitude of the emissions sampling apparatus 10, speed of the maritime vessel, and heading of the maritime vessel, fuel type being used and other information associated with the exhaust of the maritime vessel. Additionally, other gas values such as methane, nitrogen dioxide, nitrogen oxide, carbon monoxide, and hydrocarbons can also be sent.

The latitude and longitude data, date, time, altitude, heading and speed of the maritime vessel can be supplied the GPS system 16.

The sulfur dioxide values, carbon dioxide values, and any of the values of methane, nitrogen dioxide, nitrogen oxide, carbon monoxide, and hydrocarbons are preferably raw detector values from the detector 243 behind the passband filters 248.

The gas pressure and gas temperature are preferably taken within the sample chamber 244 of the gas absorption cell 240 with sensors 251.

The gas humidity is supplied by the relative humidity sensor 250. The sulfur dioxide sensor values and carbon dioxide sensor values can be calculated by the electronic drivers and processors 18 from the readings provided by the gas absorption cell 240. The gas pressure can also be provided by the gas pressure/temperature sensor 36.

The diagnostic data can include: enclosure temperature or thermal data from a temperature sensor within the emissions sampling apparatus, battery voltage, TEG voltage, geolocation, sample gas conditioning, filter pressure present in the prefilter or the layered filter, and tamper detection count.

The enclosure temperature is taken by the internal gas pressure/temperature sensor within the emissions sampling apparatus to determine anomalies in the data may be caused by the environmental conditions that put the emissions sampling apparatus out of the thermal operating tolerances of emissions sampling apparatus.

The battery voltage and TEG voltage are measured using internal analog-to-digital (ADC) converters to monitor thermal energy harvesting effectiveness and battery capacity and degradation.

The filter pressure is a measure of the difference in vacuum pressure in the gas path prior to vacuum pumping gas for the sample and immediately after pumping which can show trends of the filter clogging over time. Gas pressure sensors can be present in the exhaust 219 or the intake 207 of the layered filter 34. Additionally, pressure/temperature sensor 36 can be used.

The tamper count is indicative of whether the housing of the emissions sampling apparatus 10 has been removed or opened and is a tally of the number of times a light detector is exposed to light that indicates if the emissions sampling apparatus has been opened since manufacture, which would cast doubt on the values after an increase in the count. It is noted that if the tamper detection count is triggered, data is still collected but is flagged as possibly being defective.

It is noted that there is no connection to the ship data system for either data collection or transmission of the data to the monitoring center 30.

The data provided to the monitoring center 30 can be supplemented with additional ship data. For example, noon reports can be obtained to provide additional data for understanding fuel consumption and associated weather conditions the maritime vessel is in or was in during specific fuel consumption.

The diagnostic data is used to determine whether the emissions sampling apparatus 10 is functioning correctly, whether the emissions sampling apparatus 10 has been tampered with or whether the emissions sampling apparatus 10 should be replaced prior to device end-of-life.

The monitoring system of the monitoring center 30 extracts the data and stores the data in a repository (step 902).

The monitoring system then calculates the carbon emissions rate over distance and time and stores the carbon emission rate in the repository (step 903).

The monitoring system calculates the sulfur emissions rate in the fuel level at a specific location and stores the sulfur emission rate and the specific location of the maritime vessel in a repository (step 904).

The monitoring system determines if the specific location of the maritime vessel is in a regulated zone (step 905). The regulated zones are defined by a list of latitude and longitudinal coordinates that delineate the boundaries. For example, geofences can be used to determine if each sample is taken within or outside of any boundary.

If the specific location of the maritime vessel is in a regulated zone (step 906), and the sulfur emissions rate is within an expected range for the regulated zone (step 907), the monitoring system sends a notification regarding the sulfur emissions rate being within the expected range and fuel compliance of the maritime vessel to users (step 908) and the method ends. The calculation of the sulfur levels and their associated limits in specific locations is based on Regulation 14 of MARPOL Annex VI.

The users can be owners of the maritime vessel, captain of the maritime vessel or others present on the maritime vessel, Coast Guard, other law enforcement or users monitoring fuel consumption or environmental factors, other users.

If the specific location is in a regulated zone (step 906) and the sulfur emissions rate is not within an expected range for the regulated zone (step 907), the monitoring system determines if the emissions sampling apparatus 10 is functioning correctly (step 909). The function of the emissions sampling apparatus 10 can be determined by comparing the diagnostic data to a reference point within predetermined parameters. If the monitoring system determines that the emissions sampling apparatus 10 is not functioning correctly by functioning outside of the predetermined parameters or has been tampered with (step 910), a replacement emissions sampling apparatus 10 is sent to the maritime vessel and a notification is sent to the users with the calculated sulfur emissions rate (step 911) and the method ends. The tampering of the emissions sampling apparatus can be determined by the tamper count received.

If the specific location is in a regulated zone (step 906) and the sulfur emissions rate is not within an expected range for the regulated zone (step 907), the monitoring system determines if the sulfur dioxide emissions apparatus 10 is functioning correctly (step 909). If the monitoring system determines that the emissions sampling apparatus 10 is functioning correctly and within predetermined parameters and the tamper count has not exceeded a predetermined amount (step 910), a notification regarding the calculated sulfur emissions rate and noncompliance is sent to the users (step 912) and the method ends.

If the specific location is not in a regulated zone (step 906), the method ends.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The present invention may be a system, a method, and/or a computer program product at any possible technical detail level of integration. The computer program product may include a computer readable storage medium (or media) having computer readable program instructions thereon for causing a processor to carry out aspects of the present invention.

User Interface

Figure 12:
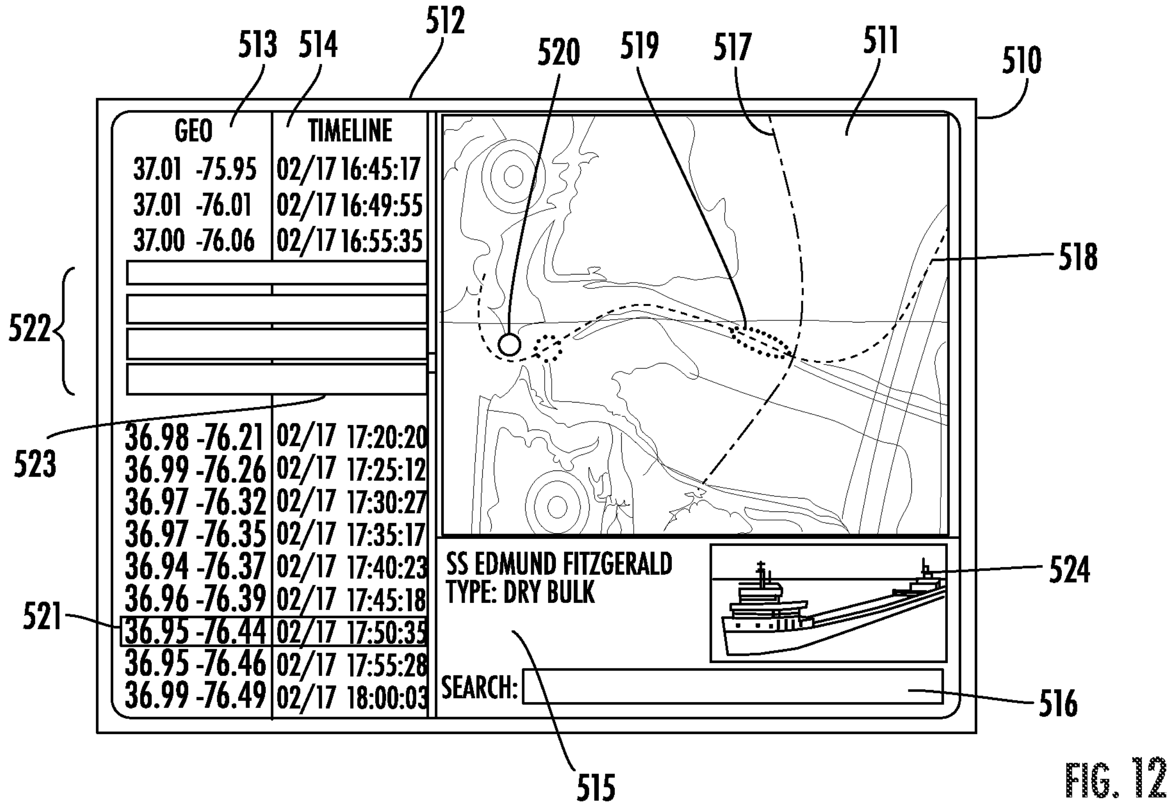
FIG. 12 shows an example user interface to convey ship data to a client.

FIG. 12 shows an example user interface to convey ship data to a client. The display may be implemented on any hardware desired, such as a tablet display 510 as shown in the figure. The example display in the figure is divided up into a time-data section 512, which has a column for geographic location (lat/lon) 513 and for time 514. A scroll bar 523 can be provided to give easy navigation through the table in a manner common to the art. An identification section 515 can be provided to display information about the identity of the vessel, which may include a picture 524 and other information, such as the "Type: Dry Bulk" note on the example display. A search box 516 may also be provided.

A map display 511 shows the path 118 of the vessel during the time interval shown on the time-data section 512. One of the time-data entries 521 is selected, and the location of the vessel on its path 518 at that time is shown by a circle 520 on the map.

The map also indicates the boundary of the SECA by a dash-dot line 517. Vessels inbound to the port are required to switch to a low-sulfur fuel before crossing the boundary of the SECA 517.

In this example, the vessel was late in switching fuels. During the time that the vessel was in the dotted portion 519 of the course line 518, it was still burning high-sulfur, which means the vessel was out of compliance during this period. The entries 522 on the time-data display 512 which correspond to this out-of-compliance period are highlighted to show the occurrence of the violation.

Alternate Embodiment

The emissions sensor apparatus 300 can use the same method of autonomous real-time sulfur dioxide and carbon dioxide monitoring of marine exhaust emissions as discussed in FIG. 7, the electronics and processors previously discussed, in addition to the user interface of FIG. 12 and sampling data collection.

Referring to FIGS. 14-18, an emissions sensor apparatus 300 is attached to at least one exhaust stack 141 of a funnel on a maritime vessel through a mounting plate 615. In this embodiment, a mounting plate 615 is fastened to an exhaust stack 141 through mounting straps 620, 621, which surround the entire outer circumference 141*a* of the exhaust stack 141 and are tightened relative to the outer circumference of the exhaust stack 141 using strap tightening nuts 622, 624, 626, 628 on anchor straps, 623 625, 627, 629, connecting the mounting straps 620, 621 to the mounting plate 615.

Figure 18:
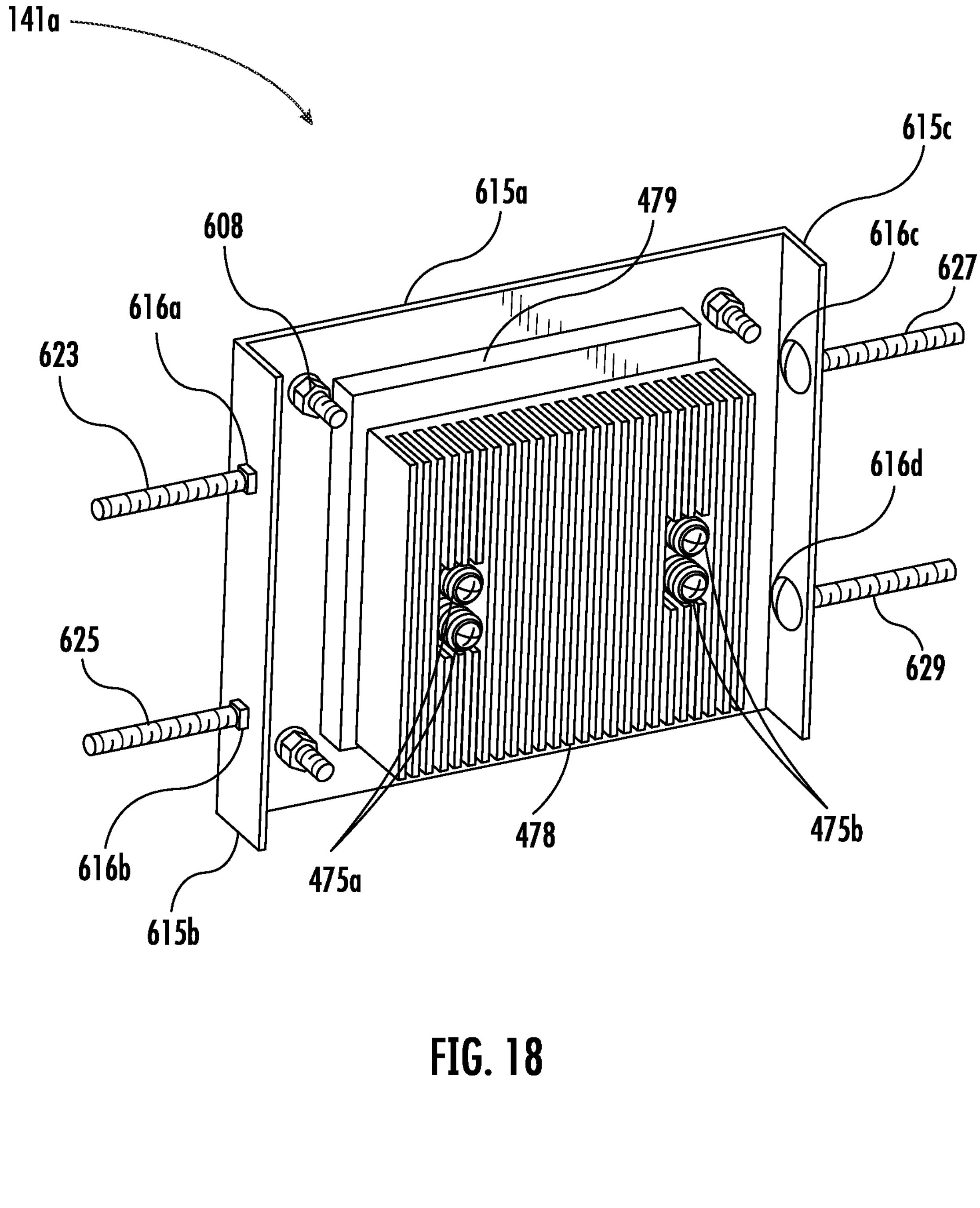
FIG. 18 shows a TEG assembly of the emissions sensor apparatus of another embodiment.

More specifically and shown in FIG. 18, the mounting plate 615 has a back plate 615*a* with a first flange 615*b* and a second flange 615*c*, opposite the first flange 615*b*. The first flange 615*b* has a first hole 616*a* and a second hole 616*b*. The first hole 616*a* of the first flange 615*b* receives a first anchor strap 623 with a first strap tightening nut 622 and connects to first end 620*a* of mounting strap 620. The second hole 616*b* of the first flange 615*b* receives a second anchor strap 625 with a second strap tightening nut 624 and connects to a first end 621*a* of mounting strap 621. The second flange 615*c* has a first hole 616*c* and a second hole 616*d*. The first hole 616*c* of the second flange 615*c* receives a third anchor strap 627 with a third strap tightening nut 626 and connects to a second end 620*b* of mounting strap 620. The second hole 616*d* of the second flange 615*c* receives a fourth anchor strap 629 with a fourth strap tightening nut 628 and connects to the second end 621*b* of the mounting strap 621. Mounted to the back plate 615*a* is a thermoelectric generator (TEG) assembly 450 including a heat sink 478 which will be described in further detail below.

Figure 17:
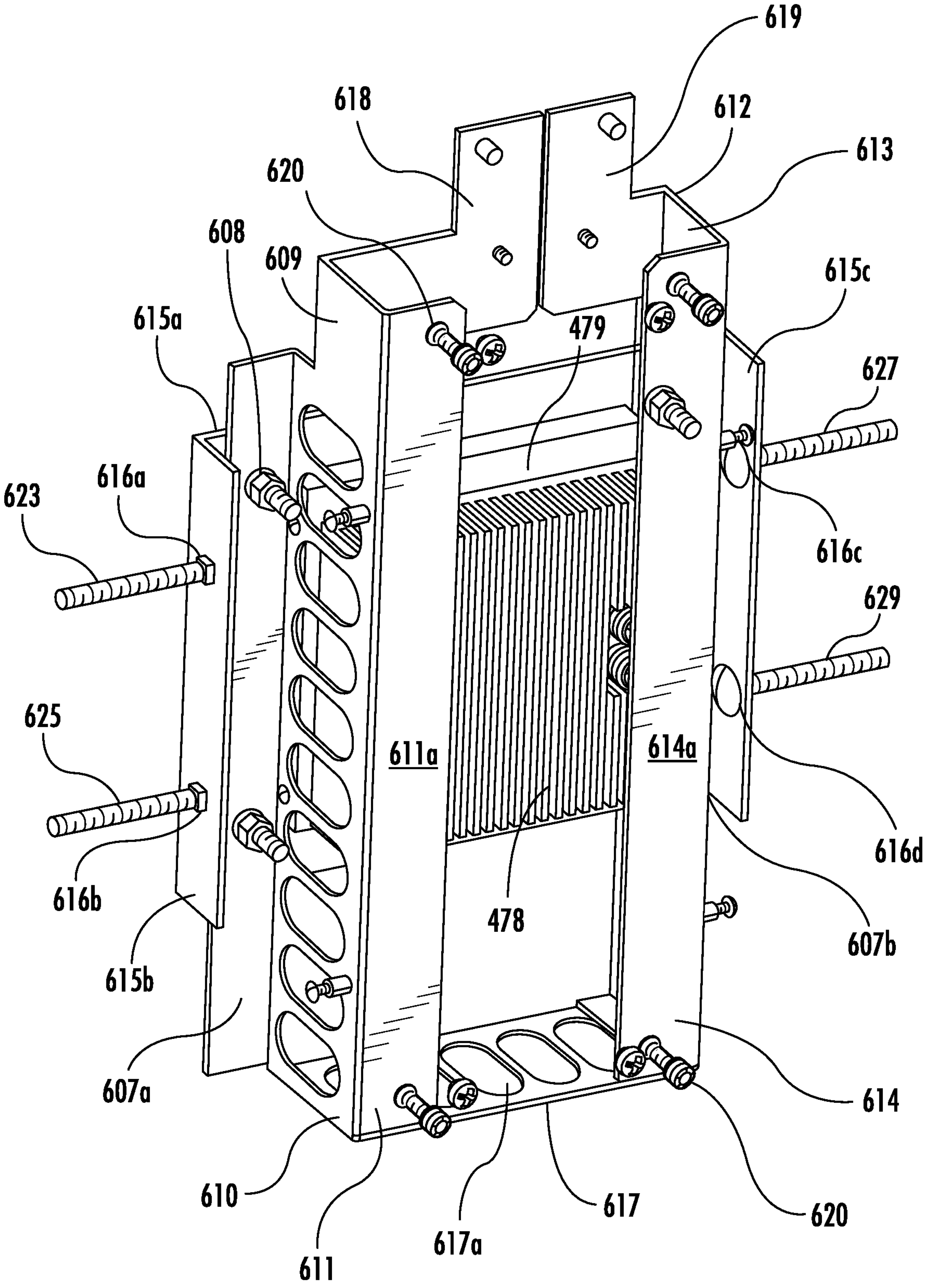
FIG. 17 shows a mounting bracket within the emissions sensor apparatus of another embodiment between the gas drying tubes and a thermoelectric generator (TEG) assembly.

Referring to FIG. 17, surrounding the TEG assembly 450 and the heat sink 478 is a heat sink housing 606. The heat sink housing 606 has a first flange 607*a* which receives bolts 608 of the back plate 615*a* and is received between the first flange 615*b* of the mounting plate 615 and a thermal block transfer 479 of the back plate 615*a*, such that the first flange 607*a* is parallel to the back plate 615*a*. A second flange 607*b* receives bolts 608 of the back plate 615*a* and is received between the second flange 615*c* of the mounting plate and the thermal block transfer 479. Connected to the first flange 607*a* of the heat sink housing 606 is an L-shaped bracket 609 with a vertical portion 610 of the "L" containing a plurality of holes 610*a* for heat dissipation and an end 610*b* of the vertical portion 610 perpendicular to the first flange 607*a*. The horizontal portion 611 of the "L" forms a flat surface 611*a* to receive housing 650 for the sensor gas device pathway. Connected to the second flange 607*b* of the heat sink housing 606 is a L-shaped bracket 612, which is a mirror image of L-shaped bracket 609. The L-shaped bracket 612 is connected to the second flange 607*b* of the heat sink housing 606. The vertical portion 613 of the "L" contains a plurality of holes 613*a* for heat dissipation. An end 613*b* of the vertical portion 613 is perpendicular to the second flange 607*b*. The horizontal portion 614 of the "L" forms a flat surface 614*a* to receive the housing 650 for the sensor gas device pathway. Connecting the L-shaped bracket 609 and the L-shaped bracket 612 is a bottom piece 617 with a series of holes 617*a* for additional heat dissipation. Parallel to the flat surface 611*a* and perpendicular to the vertical portion 610 of the L-shaped bracket 609 is inverted L piece 618. Parallel to the flat surface 614*a* and perpendicular to the vertical portion 613 is an inverted L piece 619. Both the inverted L pieces 618, 619 are opposite the bottom piece 617 and provide a flat in which a condenser chamber 400 is mounted. The condenser chamber 400 is connected to a sample gas tube 344.

Figure 16:
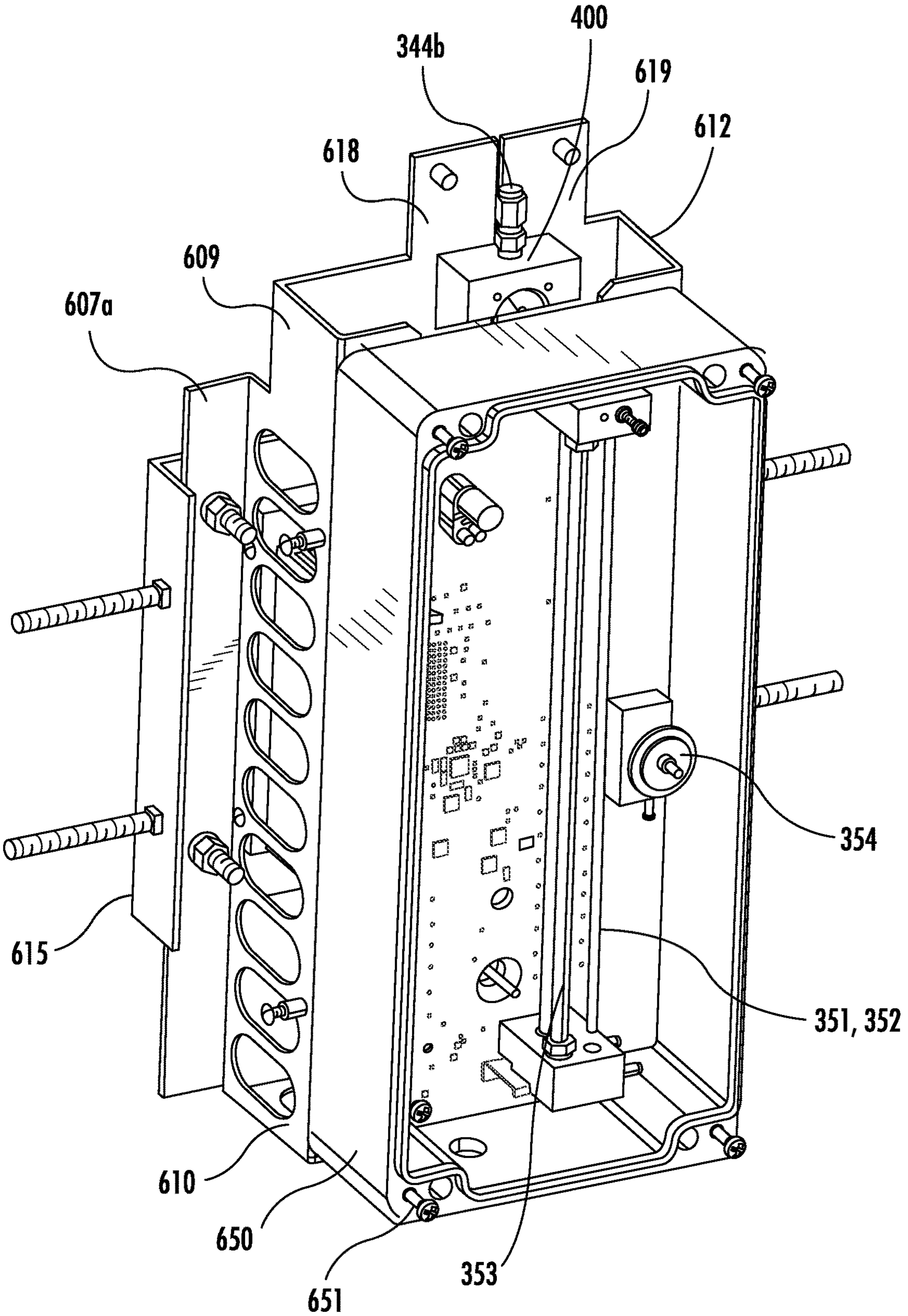
FIG. 16 shows the gas drying tubes within the emissions sensor apparatus of another embodiment.

Referring to FIG. 16, mounted and fastened to the flats 611*a*, 614*a* of the heat sink housing via bolts 620 is the housing 650 for the sensor gas device pathway. Within the housing 650 is the pump 350, gas drying tubes 351, 352, NDIR optic tube or gas absorption cell 240, temperature/humidity sensors 353, detector 243, emitter 242 and a particulate filter 355. Also present, but not shown are electronics drivers and processors 12, a satellite modem 14, a global positioning system 16, and a power management and battery back-up system 24.

Figure 15:
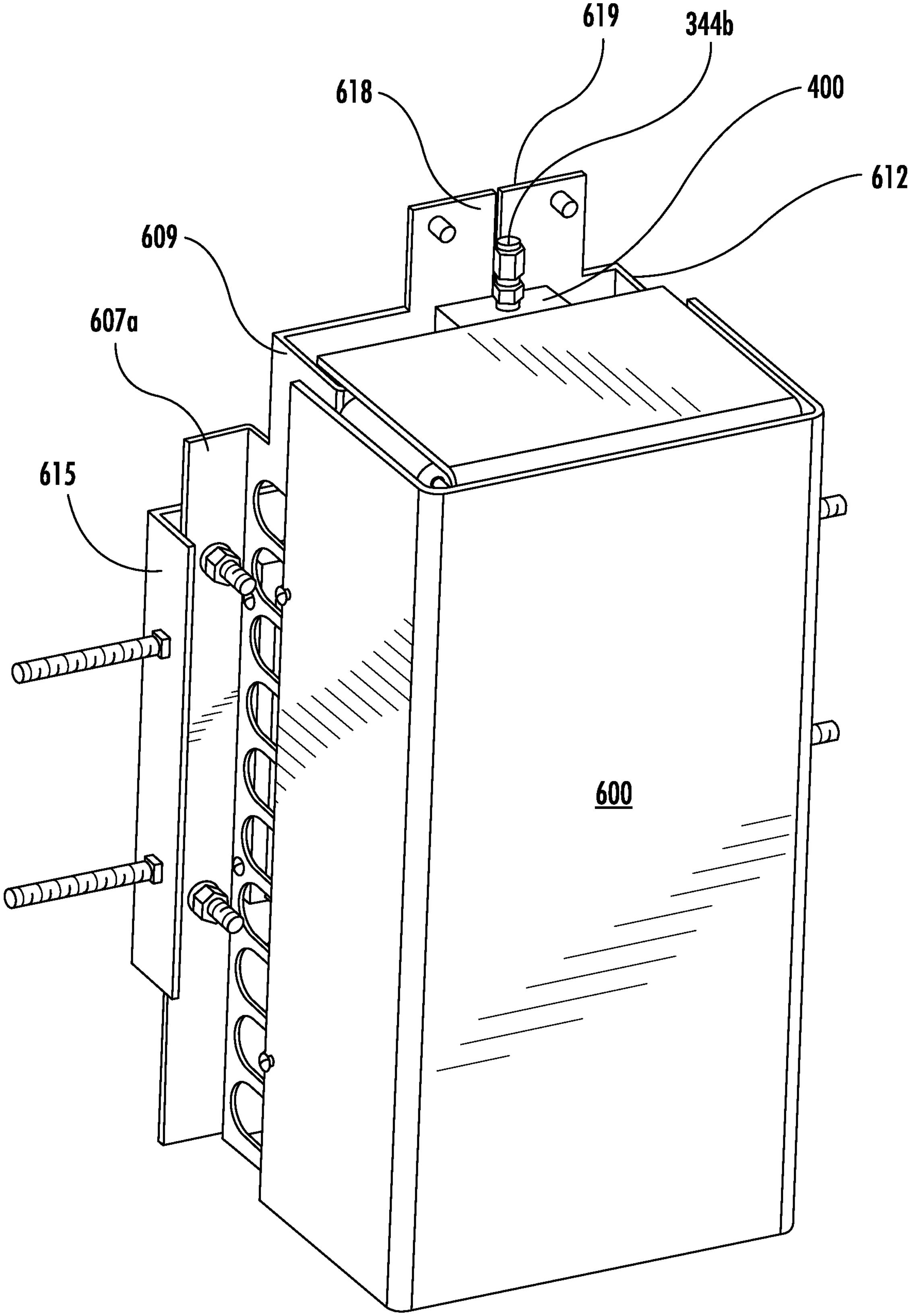
FIG. 15 shows a perspective view of the emissions sensor apparatus of another embodiment.

As shown in FIG. 15, surrounding the housing 650 and the condenser chamber 400 is an outer housing 600. The outer housing 600 engages screws 651 of the housing 650. The outer housing 600 which surrounds and protects subsystems of the apparatus from dirt, airborne dust particles (IP66 or NEMA 4× rated).

Figure 14:
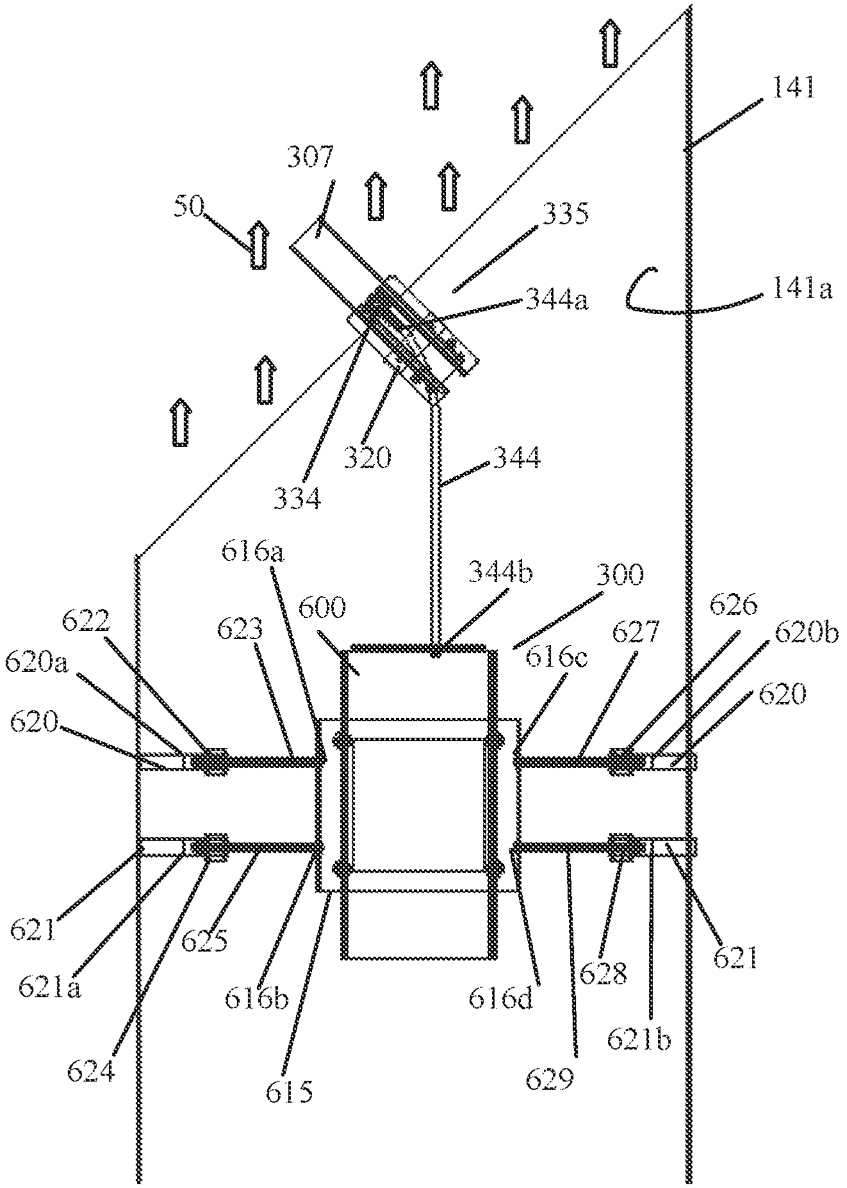
FIG. 14 shows an emissions sensor apparatus of another embodiment mounted to an exhaust stack of a marine vessel.
Figure 19:
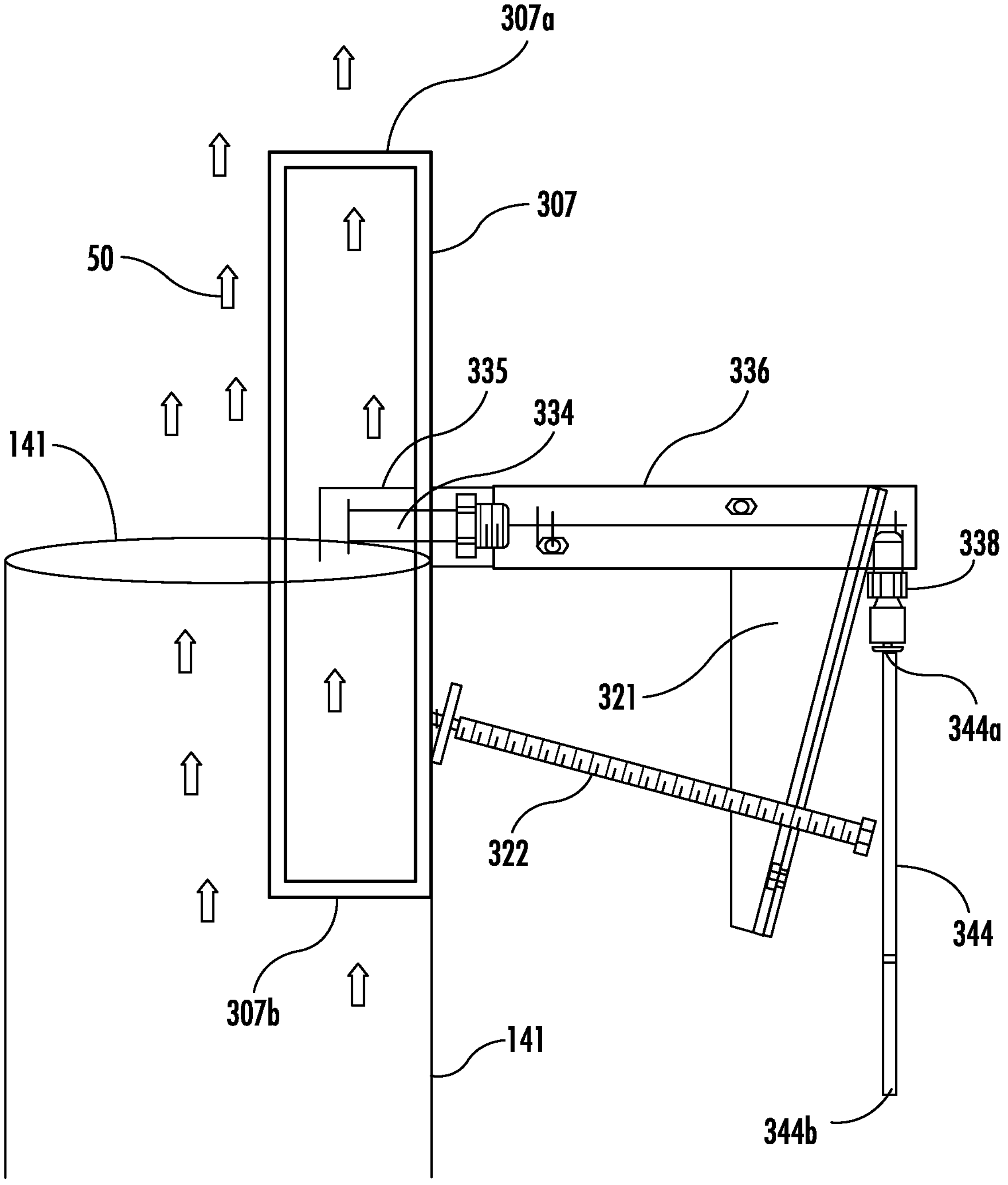
FIG. 19 shows a sectional view of the gas sample intake associated with the emissions sensor apparatus of another embodiment.

FIGS. 14 and 19 show the separate exhaust sampling apparatus 335 connected to the emissions sensor apparatus 300 via a sample gas tube 344. It is noted that the sampling apparatus 335 and the emissions sensor apparatus 300 together are considered to form the emissions sampling apparatus. The sampling apparatus 335 is mounted via clamp 320, to the outer circumference 141*a* of the exhaust stack 141 with an exhaust sample intake 307 being present within the exhaust gas 50 exiting the exhaust stack 141. The exhaust sample intake 307 is tube or other similar shape with a first open end 307*a* and a second open end 307*b*. Within the exhaust sample intake 307 is large particulate filter 334 surrounded by a filter shield 335. The filter shield 335 protects the particulate filter 334, while still allowing exhaust to enter. The particulate filter 334 is connected to the sample gas tube 344 at a first end 344*a* by a compression fitting 338 through a gas sample channel 336. The large particulate filter 344 may be porous stainless steel filter and may remove particulates which are greater than 0.05 microns.

While the clamp 320 shown to connect the sampling apparatus 335 includes a bolt frame 321 and bolt 322, other means can also be used.

Exhaust gas 50 within the exhaust stack 141 flows through the sample gas intake 344, with some of the exhaust gas 50 flowing in the large particulate filter 344. After exiting the large particulate filter 344, the exhaust gas 50 flows through the gas sample chamber 336 and to the gas sample tube 344. The exhaust gas 50 then exits the second end 344*b* of the gas sample tube 344 and flows to the condenser 400 within the emissions sensor apparatus 300.

Figure 22:
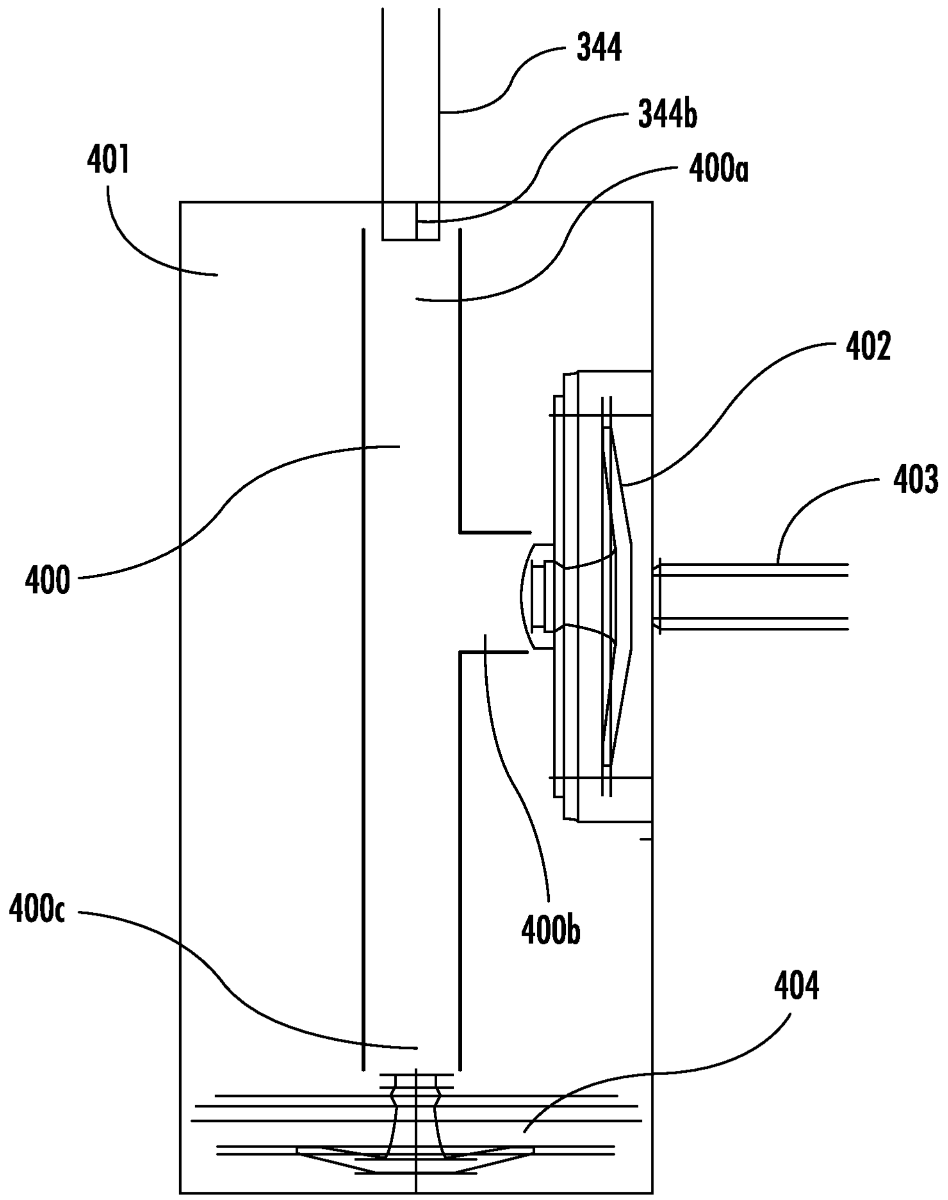
FIG. 22 shows a sectional view of the condenser chamber within the emissions sensor apparatus of another embodiment.

Referring to FIG. 22, the exhaust gas 50 enters a first end 400*a* of the condenser chamber 400 and flows to a second end 400*b* through a sample gas export umbrella valve 402 to a gas sample out tube 403 connected to gas drying tubes 351, 352 when the vacuum is drawn by the pump 350. It is noted that the sample gas export umbrella valve 402 only opens to allow exhaust gas 50 to exit when pump 350 is engaged. The exhaust gas 50 is cooled within the condenser chamber 400 by the condenser block 401 surrounding the condenser chamber 400. The condensing chamber 400 collects condensation or water inadvertently taken in through the gas sample input or second end 344*b* of the gas sample tube 344. The condensation discharge port umbrella valve 404 allows condensation to exit the condenser chamber 400 through condensation output 400*c* except when the vacuum is drawn inside the condenser chamber 400 by the pump 350.

Figure 20:
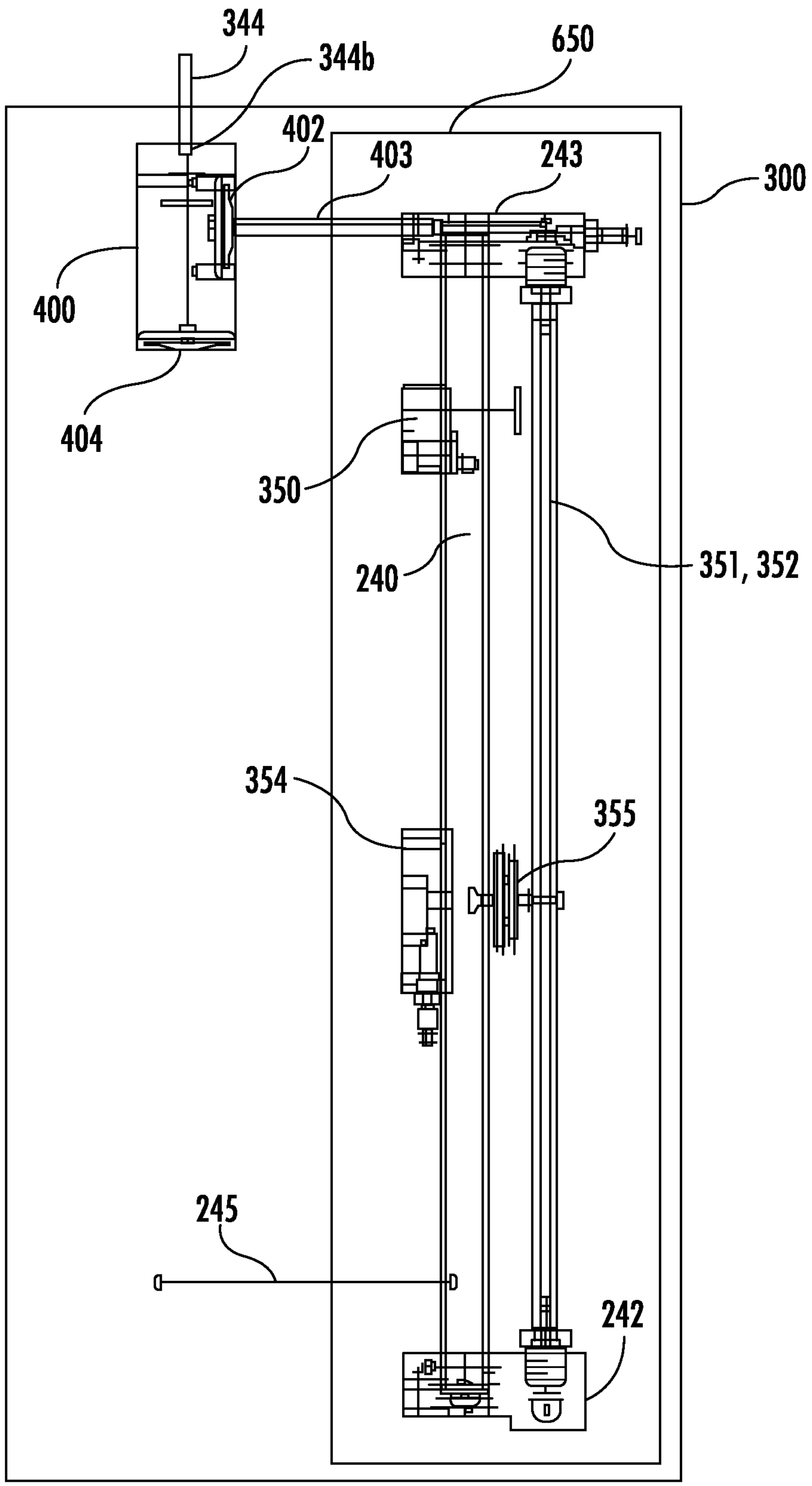
FIG. 20 shows a sensor device gas path within the emissions sensor apparatus of another embodiment.

FIG. 20 shows the sensor device gas path. Gas drying tubes 351, 352 and a NDIR optic tube or gas absorption cell 240 are present between a detector 243 and an emitter 242. Present on the gas absorption tube 245 are a pump 350 and temperature/humidity sensors 354. A fine particulate filter 355 is present between the drying tubes 351, 352 and the gas absorption cell 240. A gas exit 245 is present off of the drying tubes 351, 352.

Figure 21:
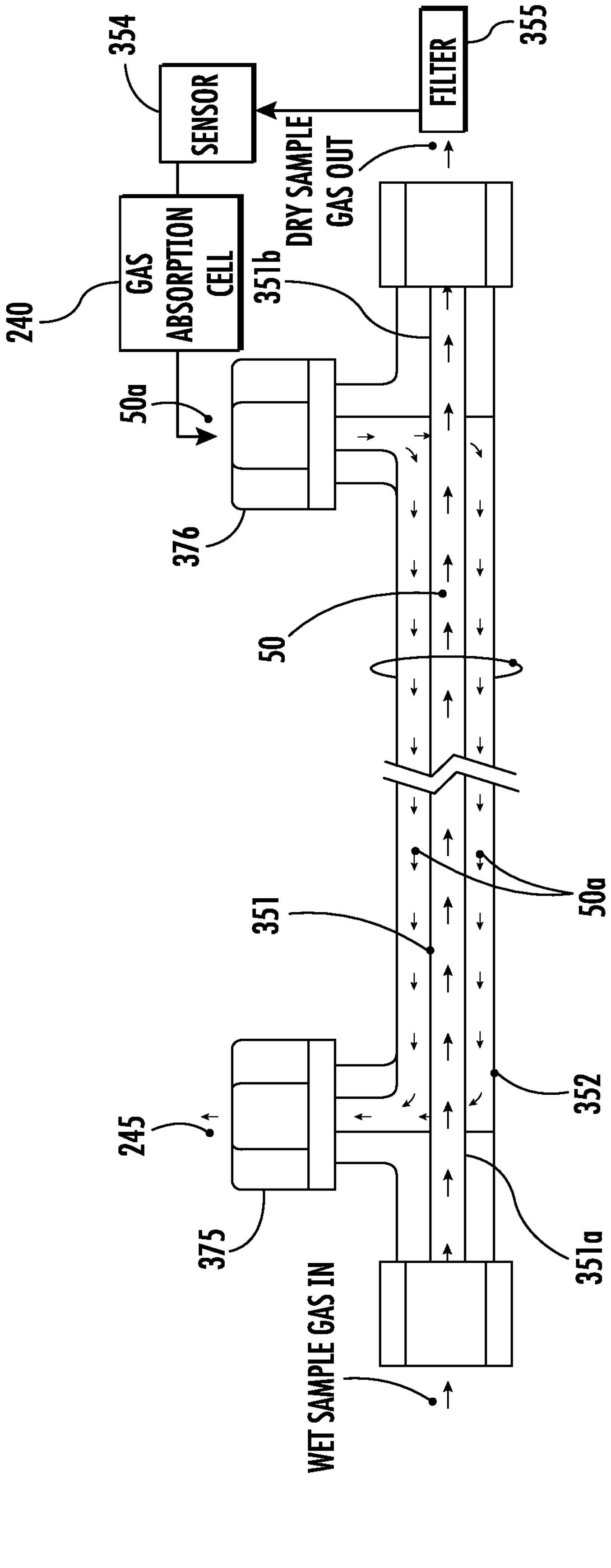
FIG. 21 shows a schematic of the gas flow within the Nafion tubing of the sensor device gas path.

The gas sample out tube 403 is connected to drying tubes 351, 352 to extract any additional moisture present within the exhaust gas sample. The gas drying tube 351 is a hollow tube preferably made of a polymer that allows water vapor to pass through the polymer walls of the hollow tube as shown in FIG. 21. The gas drying tube 351 is preferably Nafion™ tubing, although other tubing could also be used. The gas drying tube 351 is surrounded by a hollow tube or shell 352. The gas drying tube 351 has a first end 351*a* for receiving a wet sample exhaust gas 50 and a second end 351*b* for outputting a dry exhaust sample gas 50.

After the exhaust gas sample 50 exits the gas drying tube 351, the gas moves through a fine particulate filter 355 and passes over the humidity, temperature and pressure sensors 354 to the gas absorption cell 240. The gas absorption cell 240 utilizes non-dispersive infrared absorption spectrometry (NDIR-AS) is shown in FIG. 6. From the exhaust 219 of the exhaust flange 218, exhaust gas vapor passes into the intake port 241 of the gas absorption cell 240. After the exhaust gas sample has passed through the exhaust gas vapor 50 exits the gas absorption cell 240 and flows into the dry purge gas in 376 near the second end 351*b* of the gas drying tube 351. The exhaust gas 50*a* is pumped by pump 350 within the shell to the wet purge gas out 375 near the first end 351*a* of the gas drying tube 351.

The partial pressure of the water vapor in the dry purge gas 50*a*, equivalent to the dried exhaust gas is less than in the sample exhaust gas 50, such that water vapor present in the gas drying tube 351 in the exhaust gas sample 50 transfers through the polymer of the gas drying tube 351 and into the purge gas path within the shell 352 prior to exiting to the second end 351*b*. From the wet purge gas out 375, fluid flows to the gas exit 245 and exits the emissions sampling apparatus 300.

Figure 23:
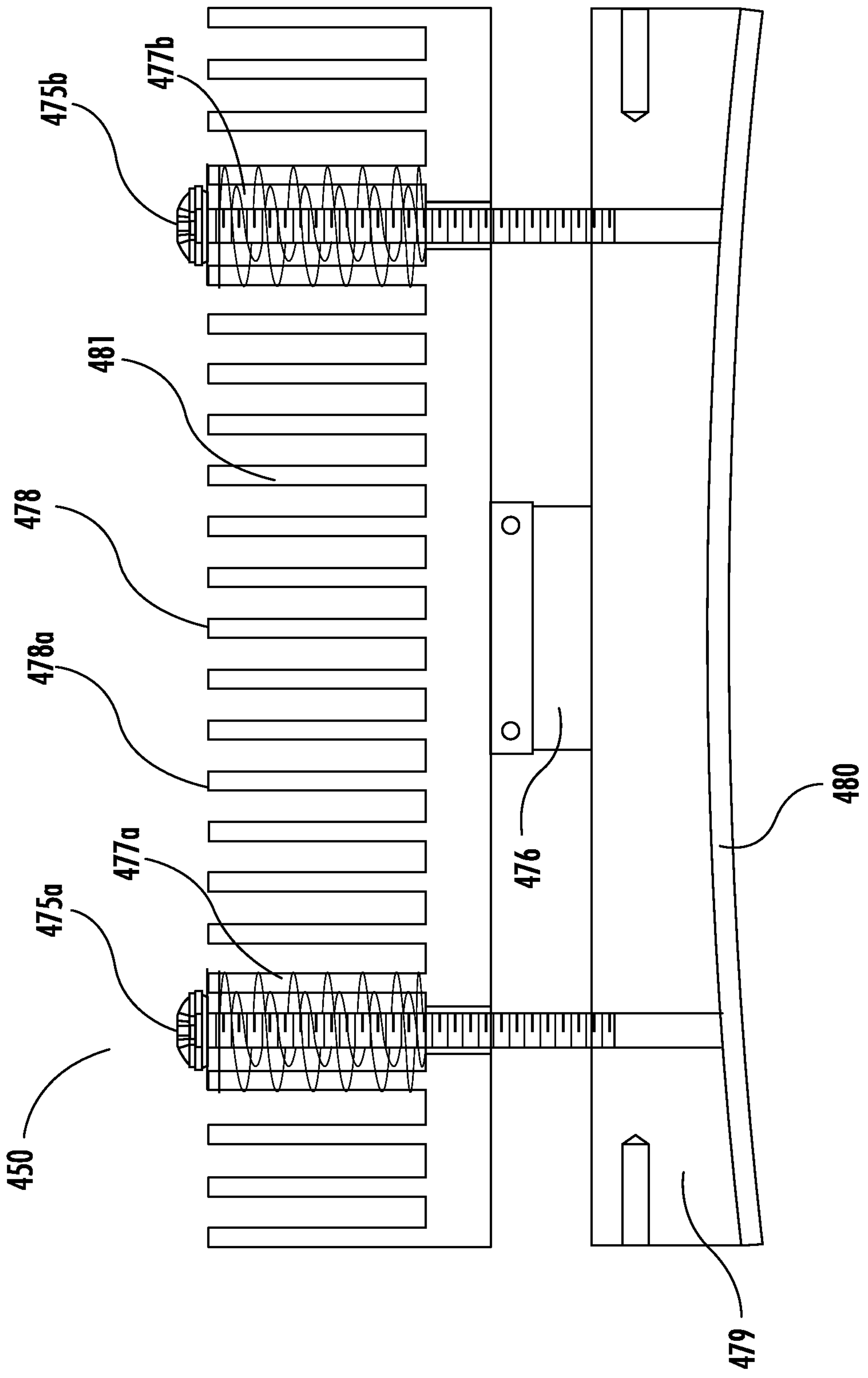
FIG. 23 shows a sectional view of the TEG assembly of the emissions sensor apparatus of another embodiment.

FIG. 23 shows a thermoelectric generator assembly.

Within the heat sink housing 606 is a thermo-electric generator (TEG) 450, and a heat sink 478. The output of the TEG 450 and heat sink 478 is a power source connector (not shown) supplying power to the power management and back-up system 24 to power the emissions sampling apparatus 300.

Heat from the exhaust stack 141 is absorbed through the thermal transfer pad 480. The thermal transfer pad 480 is a pliant, adhesive material and can accommodate variations in the expected diameter of the exhaust pipe 141 to maximize heat transfer to the thermal transfer block 479. The thermal transfer pad 480 is attached to the thermal transfer block 479. The thermal transfer block 479 is curved to accommodate the curvature of the expected exhaust stack 141 diameter and carry the hear through to a surface area that matches the size of the TEG 476. It is noted that the narrowing of the thermal transfer block 479 allows a layer of insulation or heat shield that blocks radiant heat directly onto the heat sink 478.

The thermal transfer block 479 is connected to a heat sink 478 through the TEG 450. The heat sink is secured to the thermal transfer block 479 by a first pair of screws 475*a* and a second pair of screws 475*b*. The screws 475*a*, 475*b* compress springs 477*a*, 477*b* present between the pairs of screws 475*a*, 475*b* and the heat sink 478 to hold the TEG 450 between the heat sink 478 and the thermal transfer block 479. The springs 477*a*, 477*b* apply a strong pressure to enhance thermal transfer through the TEG 450 that yields to the thermal expansion and contraction of the heat sink 478 and the thermal transfer block 479 and protects the TEG 450 from damage.

The heat sink 478 has a "cold" or heat dissipation side 478*a* that dissipates the heat through a large surface areas of the fins 481. It is noted that the fins 481 are cut away in a manner so as to allow the springs 477*a*, 477*b* to contact a flat surface.

The TEG 476 produces adequate power based on the thermal differentials seen between the thermal transfer block 479 and the heat sink 478 when mounted to the outer circumference 141*a* of the exhaust stack 141. The heat sink 478 draws heat from the TEG 476. In other words, the TEG 476 generates power while cooling and dissipation of heat through the heat dissipation side 478*a* of the heat sink 478 to create electrical potential which can be stored and transferred to the power management and battery back-up system 24 and/or directly to power the emissions sampling apparatus 300 via the wires (not shown).

The power management and battery backup system 24 controls the battery charging from the TEG 476 according to the voltage and environmental specifications of the battery of the emissions sampling apparatus 10. A state of charge calculation based on voltage and current flow monitoring over time and temperature is conducted by the power management and battery backup system 24. The state of charge value allows alerts to be triggered when the battery is in defective or low charge state.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An emissions sampling apparatus for sampling from an exhaust stack of a maritime vessel comprising:

an exhaust sample intake apparatus mounted within the exhaust stack comprising: an exhaust inlet for receiving exhaust gas from within the exhaust stack; an exhaust sample particulate filter within the exhaust inlet for removing particulates from the exhaust gas; a gas sample channel connected to an exhaust sample particulate filter outlet; and a gas sample tube with a first end connected to the gas sample channel and a second end;

an emissions sensor apparatus mounted to an outer circumference of the exhaust stack of the maritime vessel, the emissions sensor apparatus comprising:

a) a condenser connected to the second end of the gas sample tube to separate and discharge condensate from the exhaust gas, the condenser comprising: a condenser chamber having a gas input, a gas output and a condensation output; a condenser block surrounding the condenser chamber to cool exhaust gas in the condenser chamber; an exhaust gas export valve connected to the gas output of the condenser chamber; and a condensation discharge port valve connected to the condensation output to remove condensate from the exhaust gas;

b) a gas drying tube connected to the gas output of the condenser chamber, the gas drying tube comprising: a first hollow tube having a first hollow tube inlet connected to the gas output of the condenser chamber and a first hollow tube outlet connected to a particulate filter; and a second hollow tube surrounding the first hollow tube, the second hollow tube having a second hollow tube inlet and a second hollow tube outlet connected to a gas exit;

c) at least one gas absorption cell for determining sulfur dioxide and carbon dioxide levels within the exhaust gas having an inlet connected to the outlet of the particulate filter and an exhaust outlet for exhausting gas to the second hollow tube inlet of the gas drying tube, the gas absorption cell having a first end with an emitter comprising a reflector and an infrared source, a second end with at least one detector and at least two passband filters with one of the passband filters specific to carbon dioxide and another of the passband filters specific to sulfur dioxide, the first end of the gas absorption cell and the second end of the gas absorption cell being separated by a sample gas chamber extending a length between the first end of gas absorption cell and the second end of gas absorption cell;

d) a pump for pumping the exhaust gas from the exhaust gas of the maritime vessel through the exhaust sample intake, the condenser, the first hollow tube of the gas drying tube, the particulate filter, the gas absorption cell, the second hollow tube of the gas drying tube and out the exhaust outlet; wherein the exhaust gas from the exhaust outlet of the at least one gas absorption cell is pumped by the pump through the second hollow tube to the gas exit, such that a water vapor content of the exhaust gas pumped through the second hollow tube has less than a water vapor content than the exhaust gas flowing through the first hollow tube, whereby the exhaust gas in the first hollow tube transfers water vapor through walls of the first hollow tube to the exhaust gas in the second hollow tube drying the exhaust gas; wherein exhaust gas from the first hollow tube outlet contains less water vapor than the exhaust gas at the first hollow tube inlet;

e) a processor for receiving sulfur dioxide and carbon dioxide levels from the gas absorption cell and for controlling the pump; and f) a thermoelectric generator assembly harvesting energy from heat off of the exhaust stack, the thermoelectric generator assembly comprising: a thermal transfer pad having a first side adjacent the outer circumference of exhaust stack and a second side; a thermal transfer block attached to the second side of the thermal transfer pad; a heat sink comprising a plurality of fins on a dissipation side; a thermoelectric generator between the heat sink and the thermal transfer block; at least one screw securing the heat sink to the thermal transfer block; and a spring between the at least one screw and the heat sink.

2. The emissions sampling apparatus of claim 1, further comprising a modem in communication with the processor.

3. The emissions sampling apparatus of claim 1, wherein the passband filter for sulfur dioxide is 7.3 microns and the passband filter for carbon dioxide is 4.45 microns.

4. The emissions sampling apparatus of claim 3, wherein the passband filter further comprises a sulfur dioxide reference filter of 7.85 microns and a carbon dioxide reference filter of 4.65 microns.

5. The emissions sampling apparatus of claim 1, further comprising a power management system and battery backup within the housing and in communication with the processor, the pump and the thermoelectric generator assembly.

6. The emissions sampling apparatus of claim 1, wherein the first hollow tube is made of a porous polymer.

7. The emissions sampling apparatus of claim 1, wherein the emissions sensor apparatus further comprises a mounting flange adjacent the outer circumference of the exhaust stack, the mounting flange receiving the thermoelectric generator assembly and having a first flange and a second flange each defining holes.

8. The emissions sampling apparatus of claim 7, wherein the holes of the first flange each receive first anchor straps with strap tightening nuts and the holes of the second flange each receive second anchor straps with strap tightening nuts, the first anchor straps and the second anchor straps being connected to straps which surround the outer circumference of the exhaust stack to attach the emissions sampling apparatus to outer circumference of the exhaust stack.

9. The emissions sampling apparatus of claim 7, further comprising a heat sink housing mounted on top of the mounting flange and between the first flange and the second flange of the mounting flange, the heat sink housing comprising:

a first heat sink flange;

a first L-shaped bracket having a vertical portion defining a plurality of holes, connected to and perpendicular to the first heat sink flange and a horizontal portion forming a flat surface;

a second heat sink flange;

a second L-shaped bracket having a vertical portion defining a plurality of holes, connected to and perpendicular to the second heat sink flange and a horizontal portion forming a flat surface;

a bottom bracket piece connecting the first L-shaped bracket to the second L-shaped bracket; and a first inverted L-shaped piece connected to and perpendicular to the vertical portion of the first L-shaped bracket; and a second inverted L-shaped piece connected to and perpendicular to the vertical portion of the second L-shaped bracket.

10. The emissions sampling apparatus of claim 9, further comprising a housing mounted to the flat surface of the first L-shaped bracket and the flat surface of the second L-shaped bracket, the housing surrounding the pump, the gas drying tube, the gas absorption cell, and the processor.

11. The emissions sampling apparatus of claim 10, further comprising an outer housing received over the housing.

12. The emissions sampling apparatus of claim 7, wherein the condenser is mounted to the first inverted L-shaped piece and the second inverted L-shaped piece.

13. The emissions sampling apparatus of claim 1, further comprising a second gas absorption cell serially connected to the at least one gas absorption cell for determining levels of at least two gases selected from a group consisting of methane, nitrogen dioxide and hydrocarbons, the second gas absorption cell comprising: an inlet connected to the outlet of the at least one gas absorption cell, the second gas absorption cell having a first end with an emitter comprising a reflector and an infrared source, a second end with at least one detector and at least two passband filters with one of the passband filters specific to methane or nitrogen dioxide and another of the passband filters specific to hydrocarbons, the first end of the second gas absorption cell and the second end of the second gas absorption cell being separated by a sample gas chamber extending a length between the first end of the second gas absorption cell and the second end of second gas absorption cell.

14. The emissions sampling apparatus of claim 13, wherein the hydrocarbons comprises ethane, propane, isopropane and butane.

* * * * *